United States Patent
Lewis

(10) Patent No.: US 7,516,641 B2
(45) Date of Patent: *Apr. 14, 2009

(54) FLOW SENSOR METHODS AND APPARATUS

(75) Inventor: Darren F. Lewis, Anacortes, WA (US)

(73) Assignee: Upchurch Scientific, Inc., Oak Harbor, WA (US)

( * ) Notice: Subject to any disclaimer, the term of this patent is extended or adjusted under 35 U.S.C. 154(b) by 118 days.

This patent is subject to a terminal disclaimer.

(21) Appl. No.: 11/404,537

(22) Filed: Apr. 14, 2006

(65) Prior Publication Data

US 2006/0272385 A1    Dec. 7, 2006

Related U.S. Application Data

(63) Continuation-in-part of application No. 10/851,728, filed on May 21, 2004, now Pat. No. 7,055,366.

(51) Int. Cl.
*G01F 1/68* (2006.01)
*G01F 25/00* (2006.01)

(52) U.S. Cl. ..................... 73/1.16; 73/204.14
(58) Field of Classification Search ............ 73/1.16, 73/204.14, 1.34, 227; 702/100
See application file for complete search history.

(56) References Cited

U.S. PATENT DOCUMENTS

| 4,335,605 | A | | 6/1982 | Boyd |
|---|---|---|---|---|
| 5,218,866 | A | | 6/1993 | Phillips et al. |
| 5,337,603 | A | * | 8/1994 | McFarland et al. ............ 73/202 |
| 5,369,603 | A | * | 11/1994 | Myers .......................... 702/86 |
| 5,419,190 | A | | 5/1995 | Boyd |
| 5,576,487 | A | | 11/1996 | Gimson |
| 5,837,903 | A | | 11/1998 | Weigand |
| 6,352,001 | B1 | | 3/2002 | Wickert et al. |
| 6,378,354 | B1 | | 4/2002 | Sharp |
| 6,404,344 | B1 | | 6/2002 | Young |
| 6,616,823 | B2 | | 9/2003 | Kopf-Sill |
| 2004/0055374 | A1 | | 3/2004 | Cohen et al. |
| 2004/0118403 | A1 | | 6/2004 | O'Conner et al. |
| 2004/0144169 | A1 | | 7/2004 | Popielas et al. |

FOREIGN PATENT DOCUMENTS

GB    2195448 A    4/1988

OTHER PUBLICATIONS

Teledyne Hastings Instruments Application Notes: Improving Accuracy in Analog Mass Flow Measurements 5th. Order Polynomical Curve Fitting, Internet Publication.

* cited by examiner

*Primary Examiner*—Hezron E. Williams
*Assistant Examiner*—John Fitzgerald
(74) *Attorney, Agent, or Firm*—Vinson & Elkins L.L.P.

(57) ABSTRACT

Apparatus and methods of calibrating a microfluidic flow sensor, in which the flow of a fluid through a flow sensor is stopped and a first value is read from the flow sensor, then the fluid is pumped through the flow sensor sequentially at first and second selected rates, and readings from the flow sensor of the flow rate are taken for each of the rates. The readings are used in a polynomial equation to determine the actual flow rate, which is used to calibrate the sensor. The flow sensor can be connected to a computer programmed to perform the calibration method, determine the actual flow rate of the sensor, and make appropriate adjustments to the flow rate of a pump.

6 Claims, 30 Drawing Sheets

Nano-Flow System controller firmware V1.4 for 100ul pump
Code examples for microcontroller Darren Lewis, Upchurch Scientific Inc., Oak Harbor, WA 98277

The Main execution loop
```
main()
{
char *a_buffer[10];
int j;
float old_rate=0,new_rate=0;
int32 k=0;
```

Setup the microcontroller
```
clear_buffer(a_buffer,10);

disable_interrupts(global);

enable_interrupts (INT_EXT);
enable_interrupts (INT_EXT1);
enable_interrupts (INT_EXT2);
enable_interrupts (INT_RDA);

setup_timer_2(T2_DISABLED,1,1);
setup_timer_1(T1_DISABLED);
setup_timer_0(RTCC_OFF);

setup_adc(ADC_CLOCK_INTERNAL);
setup_adc_ports(RA0_RA1_RA3_ANALOG);
set_adc_channel(1);

disable_interrupts (INT_RB);
disable_interrupts (INT_PSP);
disable_interrupts (INT_AD);
disable_interrupts (INT_EEPROM);
disable_interrupts (INT_TBE);
disable_interrupts (INT_CCP1);
disable_interrupts (INT_CCP2);
disable_interrupts (INT_TIMER1);

ext_int_edge( 0, H_TO_L);
    ext_int_edge( 1, H_TO_L);
    ext_int_edge( 2, H_TO_L);

enable_interrupts(global);
```

Setup the flow sensor
```
setup();
delay_ms(250);
```

The main event loop
```
while(1) (infinite loop)
{
delay_ms(10);
```

Figure 7A

```
    output_low(LED1);
```

Read current position from the motor driver
```
if(lynx_data_ready==TRUE)
    {
        dispatch(com_1_rec_buf,COM1);
        clear_buffer(com_1_rec_buf,25);
        lynx_data_ready=FALSE;
    }
```

Read the current raw flow rate from Flow Sensor
```
if(flow_data_ready==TRUE)
    { flow_data_ready=FALSE;
        flow_rate_sum=0;

averaging_buffer[flow_rate_index]=flow_rate;
        flow_rate_index++;
        if(flow_rate_index>time_constant)
        {
            flow_rate_index=0;
            flow_rate_buf_full=TRUE;
        } for(j=0;j<time_constant+1;j++)
        flow_rate_sum+=(int32)(averaging_buffer[j]);
        avg_flow_rate=(int16)(flow_rate_sum/(int32)(time_constant+1));//Get ave.
flow rate (raw)
```

Figure 7B

Get the interpolated flow rate from the quadratic equation and the averaged raw sensor reading (useful for display purposes because it is filtered using a running average)

```
        averaged_rate=(float)return_actual_rate(avg_flow_rate);//Get ave. flow
rate (fit to cal curv
```

Get the interpolated flow rate from the quadratic equation and the instantaneous raw sensor reading (used for feedback purposes).

```
        new_rate=(float)return_actual_rate(flow_rate);//Get instantaneous flow
rate (fit to cal curve)

new_rate=(old_rate+new_rate)/(float)2;

old_rate=new_rate;
```

Perform proportional-integral-derivative (PID) on the interpolated flow sensor reading. This function provides the negative feedback. In this instance, the feedback is performed within the quadratic part of the sensor response (below 5 microlitres per minute). If the piston position reaches the end of stroke, the forward velocity is set to 0. If the position is at the beginning of stroke, the reverse velocity is set to 0.

```
        if(!calibrating&&!do_home)//Don't do if calibrating or homing...
```

```
            {
                if(!waiting)
                {
                    if((speed<5000)&&(speed>=0))
                        applied_speed=do_pid((float)speed,(float)new_rate);
```
...The PID compensator
```
                    else
                        applied_speed=speed;
```
...set applied speed to no feedback if operating above 5ul/min or below 0
```
                    if((applied_speed>=0)&&(position<=100000))
                        adjust_speed(applied_speed);
                    else
                    if((applied_speed<0)&&(position>=0))
                        adjust_speed(applied_speed);//use applied speed if moving in
reverse
                    else
                        adjust_speed(0);
                }
                else
                    adjust_speed(0);

}
            else
                adjust_speed(applied_speed);
```
...apply the no-feedback speed if calibrating or homing

```
        actual_rate=applied_speed;//added if(transmit==TRUE)
        report_values();
        delay_ms(50);
        get_position();//get the current position
        delay_ms(50);
    }
```

Figure 7C

Interpret commands from the user, if any...
```
if(host_data_ready==TRUE)
    {
        strcpy(a_buffer,"\n\r");
        if(echo)
        com_host(a_buffer);
        dispatch(host_rec_buf,HOST);
        clear_buffer(host_rec_buf,25);
        host_data_ready=FALSE;
    }
```

If the user chooses, perform calibration
```
if(calibrating&&!do_home)
do_calibration();
else
```
If the user chooses, perform homing routine
```
if(do_home&&!calibrating)
init();
```

Blink LED when homing or calibrating...

```
if(calibrating||do_home)
output_high(LED1);
else
output_low(LED2);
```

Motion commands for remote TTL operation or automatic fill/refill...

Automatic dispense
```
if(input(PIN_D7)&&!input(PIN_D6)&&!do_home&&!calibrating)
{
    speed=(float)infusion_rate;
    switch_valve(column);
    waiting=FALSE;
}
```

Automatic fill
```
if(!input(PIN_D7)&&input(PIN_D6)&&!do_home&&!calibrating)
{
    switch_valve(fill);
    speed=(float)(withdrawal_rate);
    speed=-speed;
    waiting=FALSE;
}
```

Automatic fill/dispense cycle
```
if(do_loop)
{
    if((position>(float)99990)&&!do_home&&!calibrating)
    {
        if(am_i_filling)
        {
            adjust_speed(0);
            delay_ms(50);
            adjust_speed(0);
            for(k=0;k<10;k++)
            delay_ms(1000);

switch_valve(fill);

speed=(float)(withdrawal_rate);
            speed=-speed;
            waiting=FALSE;
            am_i_filling=FALSE;
            cycle_timer=cycle_timer+2;
            write_long_vars(addr_cyc_timer,cycle_timer);

}
    } if((position<(float)10)&&!do_home&&!calibrating)
    {
        if(!am_i_filling)
        {
            adjust_speed(0);
            delay_ms(50);
            adjust_speed(0);
            for(k=0;k<10;k++)
```

Figure 7D

```
        delay_ms(1000);

switch_valve(column);
        speed=(float)(infusion_rate);
        waiting=FALSE;
        am_i_filling=TRUE;

}
    }

} the_output=(float)read_adc()/(float)204.8;

delay_ms(10);
}
return 1;
}
```
...End of main function

Handle commands sent from user via RS-232...
```
void dispatch(char* command,char source)//Respond to input commands
{
signed int16 i=1;
char the_char=0;
char out_strings[25];
float new_position=0;
char err_in=FALSE;
int32 new_rate=0;//was float
char do_ok=0;

clear_buffer(out_strings,25);

if(source==HOST)
{
```
Received command to display data to user through RS-232 port...
```
    if(command[0]=='?')
      {
          if(command[1]=='0')
          {
             show_factors=0;
             show_pos=0;
             show_raw=0;
             show_calc=0;
             show_valve=0;
             show_infuse=0;
             show_withdrawal=0;
             show_output=0;
             do_ok=1;
          } if(command[1]=='1')
          {
             show_factors=1;
             show_pos=1;
             show_raw=1;
```

Figure 7E

```
            show_calc=1;
            show_valve=1;
            show_infuse=1;
            show_withdrawal=1;
            show_output=1;
            do_ok=1;
        }
        else
        {
            if(command[1]=='e')
            {
                show_factors=1;
                do_ok=1;
            }
            if(command[1]=='p')
            {
                show_pos=1;
                do_ok=1;
            }
            if(command[1]=='r')
            {
                show_raw=1;
                do_ok=1;
            }
            if(command[1]=='f')
            {
                do_ok=1;
                show_calc=1;
            }
            if(command[1]=='v')
            {
                do_ok=1;
                show_valve=1;
            }
            if(command[1]=='i')
            {
                do_ok=1;
                show_infuse=1;
            }
            if(command[1]=='w')
            {
                do_ok=1;
                show_withdrawal=1;
            }
            if(command[1]=='o')
            {
                do_ok=1;
                show_output=1;
            }
        }
    }
Received command to cancel display of parameters to user…
    if(command[0]=='a')
    {
```

Figure 2F

```
        {
            if(command[1]=='e')
            {
                show_factors=0;
                do_ok=1;
            }
            if(command[1]=='p')
            {
                show_pos=0;
                do_ok=1;
            }
            if(command[1]=='r')
            {
                show_raw=0;
                do_ok=1;
            }
            if(command[1]=='f')
            {
                show_calc=0;
                do_ok=1;
            }
            if(command[1]=='v')
            {
                do_ok=1;
                show_valve=0;
            } if(command[1]=='i')
            {
                do_ok=1;
                show_infuse=0;
            } if(command[1]=='w')
            {
                do_ok=1;
                show_withdrawal=0;
            } if(command[1]=='o')
            {
                do_ok=1;
                show_output=0;
            }
        }
    }
Received command to continuously send/don't send parameters to user at regular
intervals...
    if(command[0]=='b')
    {
        if(command[1]=='0')
        {
            transmit=FALSE;
            do_ok=1;
        }
        if(command[1]=='1')
        {
```

Figure 76

```
            transmit=TRUE;
            do_ok=1;
        }
    }

Received calibration command, calibration flags are set
    if(command[0]=='c')
    {
        if(command[1]=='a')
        if(command[2]=='1')
        {
            calibrating=TRUE;
            switch_valve(waste_1);
            clear_calibration_flags();
            do_ok=1;
        }
    }

Received command to echo sent characters back to the user (for cosmetic purposes)
    if(command[0]=='e')
    {
        if(command[1]=='0')
        {
            echo=FALSE;
            do_ok=1;
        }
        if(command[1]=='1')
        {
            echo=TRUE;
            do_ok=1;
        }
    }
Received command to change the motor run current
    if(command[0]=='g')
    {
            run_current=return_number(command,&err_in,1);

if(run_current>100)
            run_current=100;
            if(run_current<0)
            run_current=0;
            if(!err_in)
            {
                set_current(run_current);
                do_ok=1;
            }
    }
Received command to home the pump, resets homing flags
    if(command[0]=='h')
    {
        if(calibrating==FALSE)
        {
        do_home=TRUE;
        clear_homing_flags();
        set_position(0);
        delay_ms(50);
        set_position(0);
```

Figure 7H

```
        position=0;
        home_pin=FALSE;
        do_ok=1;
        }
    }
Received command to set automatic infusion rate
    if(command[0]=='i')
    {
        new_rate=(int32)return_number(command,&err_in,1);
        if(!err_in)
        {
            write_long_vars(addr_inf_rate,new_rate);
            write_vars(addr_inf_set,ADDRESSES_WRITTEN);
            read_long_vars(addr_inf_rate,&infusion_rate);
            do_ok=1;
        }
    }
Received command to change integral constant
    if(command[0]=='k')
    {
        ki=(float)return_number(command,&err_in,1);

if(ki>25)
        ki=(float)25;
        if(ki<1)
        ki=(float)1;

if(!err_in)
        {
            do_ok=1;
        }
    }
Received command to cycle dispense/fill continuously
    if(command[0]=='l')
    {
        if(command[1]=='o')
        if(command[2]=='o')
        if(command[3]=='p')
        {
            if(command[4]=='1')
            {
                do_loop=1;
                do_ok=1;

if(speed>0)
                am_i_filling=TRUE;
                else
                am_i_filling=FALSE;

}
        if(command[4]=='0')
            {
                do_loop=0;
                do_ok=1;
            }
        }
```

Figure 7I

```
    }
Received command to send back version number for firmware
    if(command[0]=='n')
    {
        sprintf(out_strings,"Scivex NanoFlow 1.4\r\n");
        com_host(out_strings);
    }
Received command to report piston position
    if(command[0]=='p')
    {
        sprintf(out_strings,"%ld\r\n",(int32)position);
        com_host(out_strings);
    }
Received command to report current speed
    if(command[0]=='r')
    {
        sprintf(out_strings,"%ld\r\n",(int32)speed);
        com_host(out_strings);
    }
Received command to set desired flow rate of pump if(command[0]=='s')
    {
        if(command[1]=='s')
            {
                waiting=TRUE;
                do_ok=1;
            }
        else
        {
            speed=return_number(command,&err_in,1);
            if(!err_in)
            {
                applied_speed=speed;
                do_ok=1;
                waiting=FALSE;
            }

}

//  for(i=0;i<KD_LIMIT;i++)
    //  derivative_array[i]=0.1;

}
Received command to change time constant for running average filter
    if(command[0]=='t')
    { i=(int)return_number(command,&err_in,1);

if(err_in==FALSE)
        {
        if(i<0)
        i=0;
        if(i>20)
```

write_vars(addr_time_const,i);
        read_vars(addr_time_const,&i);
        time_constant=i;
        do_ok=1;
        }
    }

Received command to immediately report parameters to user
    if(command[0]=='u')
    {
        report_values();

}
Received command to change the valve position
    if(command[0]=='v')
    {
        if(command[1]=='f')
        {
            switch_valve(fill);
            do_ok=1;
        } if(command[1]=='c')
        {
            switch_valve(column);
            do_ok=1;
        } if(command[1]=='1')
        {
            switch_valve(waste_1);
            do_ok=1;
        } if(command[1]=='2')
        {
            switch_valve(waste_2);
            do_ok=1;
        }

}
Received command to set automatic dispense rate
    if(command[0]=='w')
    {
        new_rate=(int32)return_number(command,&err_in,1);
        if(!err_in)
        {
            write_long_vars(addr_wit_rate,new_rate);
            write_vars(addr_wit_set,ADDRESSES_WRITTEN);
            read_long_vars(addr_wit_rate,&withdrawal_rate);
            do_ok=1;
        }
    }
Received command to set the first (zero flow) flow sensor response
    if(command[0]=='x')
```

Figure 17K

```
    {
        i=(int16)return_number(command,&err_in,1);
        if(!err_in)
        {
        calibration_factor[0]=i;
Recalculate quadratic based on new number
get_abc(RATE_1,RATE_2,RATE_3,calibration_factor[0],calibration_factor[1],calibra
tion_factor[2]);
        write_vars(addr_1x,calibration_factor[0]);
        write_vars(addr_cal_set,ADDRESSES_WRITTEN);
        do_ok=1;
        }
    }
Received command to set the second (moderate flow) flow sensor response if(command[0]=='y')
    {
        i=(int16)return_number(command,&err_in,1);
        if(!err_in)
        {
        calibration_factor[1]=i;
Recalculate quadratic based on new number
get_abc(RATE_1,RATE_2,RATE_3,calibration_factor[0],calibration_factor[1],calibra
tion_factor[2]);
        write_vars(addr_1y,calibration_factor[1]);
        write_vars(addr_cal_set,ADDRESSES_WRITTEN);
        do_ok=1;
        }
    }
Received command to set the third (high flow) flow sensor response
    if(command[0]=='z')
    {
        i=(int16)return_number(command,&err_in,1);
        if(!err_in)
        {
        calibration_factor[2]=i;
Recalculate quadratic based on new number
get_abc(RATE_1,RATE_2,RATE_3,calibration_factor[0],calibration_factor[1],calibra
tion_factor[2]);
        write_vars(addr_1z,calibration_factor[2]);
        write_vars(addr_cal_set,ADDRESSES_WRITTEN);
        do_ok=1;
        }
    }
Set current pump piston position
    if(command[0]=='@')
    {
        new_position=return_number(command,&err_in,1);
        if(!err_in)
        {
            set_position(new_position);
            do_ok=1;
        }
    } if(command[0]=='$')
        {
```

Figure 7L

```
            if(command[1]=='$')
            {
            cycle_timer=0;
            write_long_vars(addr_cyc_timer,0);
            do_ok=1;
            }
        }
Cancel calibration
        if(command[0]=='!')
        {
            calibrating=FALSE;
            clear_calibration_flags();

get_abc(RATE_1,RATE_2,RATE_3,calibration_factor[0],calibration_factor[1],calibra
tion_factor[2]);
            do_ok=1;
        }
        if(do_ok)
        {
            sprintf(out_strings,"OK\r\n");
            com_host(out_strings);
            //clear_buffer(com_1_rec_buf,25);//added
        }
}//end source host
if(source==COM1)
{
        position=return_humber(command,&err_in,0);//Get position information from
MicroLynx }
source=NONE;

}
Switches the valve position
void switch_valve(char a_position)
{
if(a_position==waste_1)
    {
        output_low(PIN_C3);
        output_high(PIN_C0);
        output_high(PIN_C1);
        output_high(PIN_C2);
        valve_position=1;
    } if(a_position==waste_2)
    {
        output_low(PIN_C2);
        output_high(PIN_C0);
        output_high(PIN_C1);
        output_high(PIN_C3);
        valve_position=4;
    } if(a_position==column)
    {
        output_low(PIN_C0);
```

Figure 7M

```
        output_high(PIN_C1);
        output_high(PIN_C2);
        output_high(PIN_C3);
        valve_position=3;
    } if(a_position==fill)
        {
            output_low(PIN_C1);
            output_high(PIN_C0);
            output_high(PIN_C2);
            output_high(PIN_C3);
            valve_position=2;
        }
}
```

Home the pump based on position of optical interrupt
```
void init(void)
{
int16 i=0;
char a_buffer[25];

clear_buffer(a_buffer,25);

if(!home_1&&!home_2)
    { switch_valve(waste_1);
        applied_speed=50000;

if(position>5000)
        {
            home_1=TRUE;
            set_position(150000);
            delay_ms(200);
            strcpy(a_buffer,"Finding home...\r\n");
            com_host(a_buffer);
            applied_speed=0;
            delay_ms(200);//added
            set_position(150000);//added
            delay_ms(200);//added

}

}
    else
    if(home_1&&!home_2)
    {
        switch_valve(fill);
        applied_speed=-100000;
        if(home_pin)
        {
            home_2=TRUE;
            strcpy(a_buffer,"home found...\r\n");
            com_host(a_buffer);
            applied_speed=5000;
```

Figure 7N

```
            do_home=FALSE;
            set_position(-2000);
            delay_ms(50);
            set_position(-2000);
            position=-2000;
            speed=0;
            applied_speed=0;
            do_home=FALSE;
            clear_homing_flags();
            home_pin=FALSE;
        }

}

}
```

The algorithm for finding the actual flow rate from raw sensor data in real time using the $ax^2+bx+c$ equation for a given solvent...

```
float return_actual_rate(int16 sensor_response)
{
//Roots of a quadratic...
float number=0;
float number2=0;

number=(float)sensor_response-(float)c_constant;

number2=(float)b_constant*(float)b_constant+((float)4*a_constant*(float)number)/
(float)1000;

if(number2>0)
   number2=(float)sqrt(number2);

number=((float)(-b_constant))+(float)number2;

number2=(float)((float)number/(float)((float)2*(float)a_constant))*(float)1000;

return number2;

}
```

The algorithm for finding the a, b, and c values of the quadratic from three data points collected at three different flow rates...

```
void get_abc(int16 f1, int16 f2, int16 f3,int16 r1, int16 r2, int16 r3)
{
//y=ax2 +bx +c, we want a,b,c
float number=0;
float number2=0;
char out_buf[25];

clear_buffer(out_buf,25);
```

Figure 70

```
    number=((float)r3/(float)f3)-((float)r1/(float)f3)+((float)r1/(float)f2)-
((float)r2/(float)f2);
    number2=((float)f3-(float)f2)/(float)1000;

a_constant=(float)number/(float)number2;
    b_constant=((float)r3/(float)f3)-(((float)a_constant*(float)f3)/(float)1000)-
((float)r1/(float)f3);
    c_constant=(float)r1;

}
```

The PID algorithm for pump speed control using negative feedback of actual flow sensor response...
```
float do_pid(float setpoint_speed,float measured_speed)
{
int i;

//The proportional signal
    the_proportional_error=(float)setpoint_speed-(float)measured_speed;

//The derivative average
    the_derivative_error=(float)(measured_speed-old_speed);
    old_speed=measured_speed;

if(the_derivative_error>250)
    the_derivative_error=(float)250;

derivative_array[derivative_index]=the_derivative_error;

derivative_index++;
    if(derivative_index>=KD_LIMIT)
    derivative_index=0;

the_derivative_error=0;
    for(i=0;i<KD_LIMIT;i++)
    the_derivative_error+=abs(derivative_array[i]);

the_derivative_error=the_derivative_error/(float)KD_LIMIT;

if(the_derivative_error==0)
    the_derivative_error=0.1;

the_integral_error=0;
    for(i=0;i<KD_LIMIT;i++)
    the_integral_error+=derivative_array[i];

//kd=(float)((float)250-the_derivative_error);
    kd=(float)(250)/(the_derivative_error);//was 350
    //kd=(float)((float)-0.12*the_derivative_error)+(float)40;

```
    kd=(float)40;
    if(kd<2)
    kd=(float)2;

speed_change=the_proportional_error*(float)kd;

return setpoint_speed+speed_change;

}
```

The calibration routine for determining flow sensor responses at three rates. Each of the rates are averaged for an entire turn of the pump lead screw.
```
int do_calibration(void)
{
int cal_is_done=FALSE;
char out_string[10]={'C','a','l','i',' ','D','o','n','e','\r'};
```

Set speed to 0
```
if(!cal_data_1&&!cal_data_2&&!cal_data_3)
    {
        applied_speed=RATE_1;
        cal_data_1=TRUE;
        delay_time=time+40;
    }
```
Get flow rate at no flow
```
if(cal_data_1&&!cal_data_2&&!cal_data_3)
    {
        if(time>=delay_time)
            {
                cal_data_2=TRUE;
                calibration_factor[0]=avg_flow_rate;

time_increment=0;
                delay_time=time+40;
                calibration_sum=0;
                applied_speed=RATE_2;

Set speed to moderate known level
```
if(cal_data_1&&cal_data_2&&!cal_data_3)
    {
        if(time>=delay_time)
            {
                calibration_sum+=(int32)avg_flow_rate;
                time_increment++;
```
Average flow rate for entire turn of lead screw...
```
                if(position>=required_volume)
                    {
                        cal_data_3=TRUE;
                        calibration_sum=calibration_sum/time_increment;
                        calibration_factor[1]=(int16)calibration_sum;

time_increment=0;
                        delay_time=time+40;
```

```
                        calibration_sum=0;
                        applied_speed=RATE_3;
                }
        }
        else
        required_volume=position+nl_per_turn;
    }
Set speed to known high level
if(cal_data_1&&cal_data_2&&cal_data_3)
    {
        if(time>=delay_time)
            {
                calibration_sum+=(int32)avg_flow_rate;
                time_increment++;
Average flow rate for entire turn of lead screw...
                if(position>=required_volume)
                    {
                        calibrating=FALSE;

calibration_sum=calibration_sum/time_increment;
                        calibration_factor[2]=(int16)calibration_sum;
                        applied_speed=0;
                        cal_is_done=TRUE;
                        write_vars(addr_1x,calibration_factor[0]);
                        write_vars(addr_1y,calibration_factor[1]);
                        write_vars(addr_1z,calibration_factor[2]);
                        write_vars(addr_cal_set,ADDRESSES_WRITTEN);
Calculate ax²+bx+c for the three flow sensor readings...
get_abc(RATE_1,RATE_2,RATE_3,calibration_factor[0],calibration_factor[1],calibra
tion_factor[2]);
                        com_host(out_string);
                    }
            }
        else
        required_volume=position+nl_per_turn;
    } if(cal_is_done==TRUE)
return TRUE;
else
return FALSE;
}
Send system information to the user via RS-232
void report_values(void)
{
char out_strings[25];
int i;

clear_buffer(out_strings,25);

if(show_factors)
    { for(i=0;i<3;i++)
        {
            sprintf(out_strings,"%c=%ld\r\n",i+120,calibration_factor[i]);
```

Figure 7R

```
            com_host(out_strings);
            delay_ms(5);
        }

} if(show_pos)
    {
        sprintf(out_strings,"p=%ld\r\n",(signed int32)position);
        com_host(out_strings);
    } if(show_valve)
    {
        sprintf(out_strings,"v=%d\r\n",valve_position);
        com_host(out_strings);
    } if(show_raw)
    {
        sprintf(out_strings,"r=%ld\r\n",avg_flow_rate);
        com_host(out_strings);
    } if(show_calc)
    {
        sprintf(out_strings,"f=%ld\r\n",(signed int32)averaged_rate);
        com_host(out_strings);
    } if(show_infuse)
    {
        sprintf(out_strings,"i=%ld\r\n",infusion_rate);
        com_host(out_strings);
    } if(show_withdrawal)
    {
        sprintf(out_strings,"w=%ld\r\n",withdrawal_rate);//was float
        com_host(out_strings);
    } if(show_output)
    {
        sprintf(out_strings,"o=%ld\r\n",cycle_timer);//was float
        com_host(out_strings);
    }

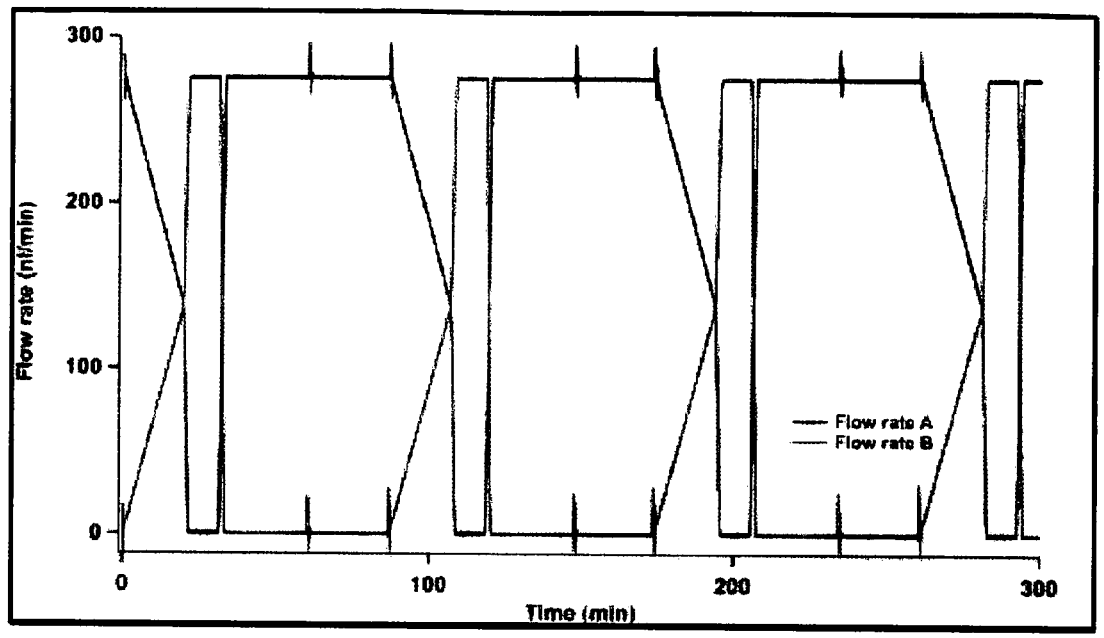
Fig. 12 Flow rates for four repeated injections on a nano-column
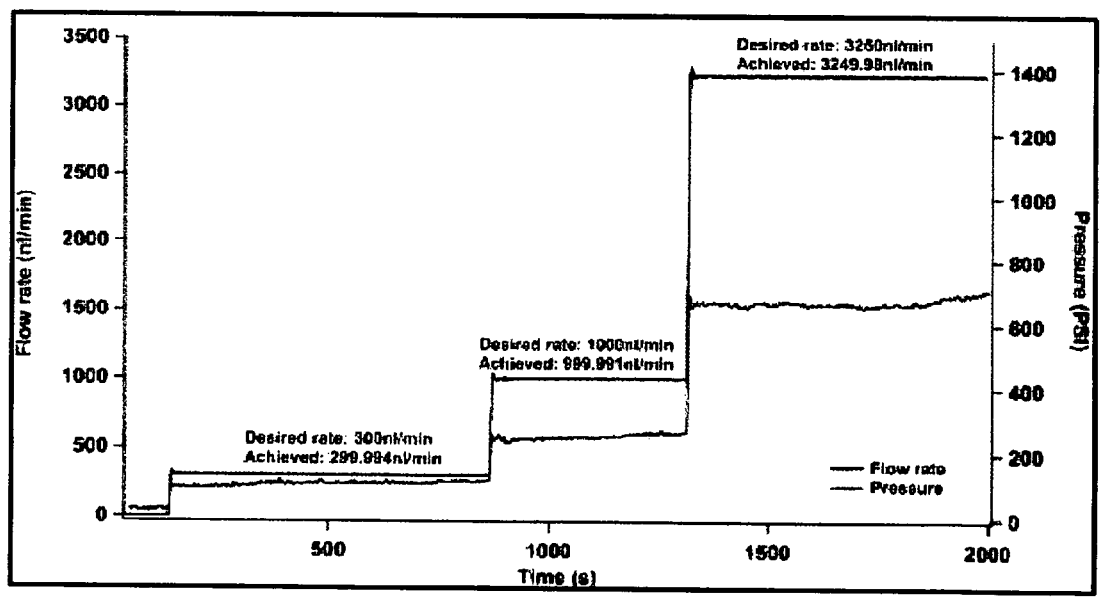
Fig. 13 Flow response for the gradient system 800 at three different rates

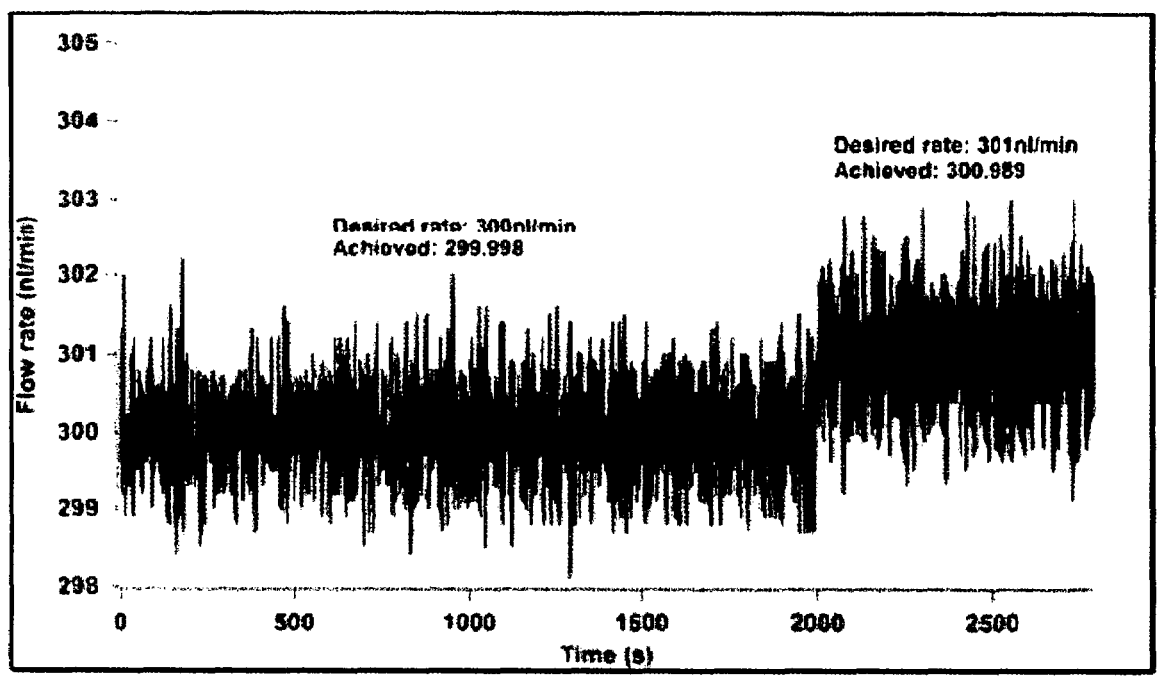
Fig. 14 A 1nl/min step increase in flow rate at 300nl/min

FLOW SENSOR METHODS AND APPARATUS

CROSS-REFERENCE TO RELATED APPLICATIONS

The application is a continuation-in-part of and claims priority to U.S. patent application Ser. No. 10/851,728, filed May 21, 2004 now U.S. Pat. No. 7,055,366, published as US 2005/0257595 A1 on Nov. 24, 2005, titled "Flow Sensor Calibration Methods and Apparatus," which is hereby fully incorporated by reference herein.

FIELD OF THE INVENTION

The invention relates to methods and apparatus for calibrating and using flow rate sensors useful in liquid chromatography, mass spectrometry, and other analytical methodologies. More particularly, the invention relates to methods and apparatus useful for the calibration and operation of ultra-low flow rate liquid sensors used in micro/nano flow chromatography, mass spectrometry and other analytical applications.

BACKGROUND OF THE INVENTION

Much of the analytical drive in biological research areas results from the desire to understand biological systems and to develop therapeutic agents for treating disease. Increasingly, worldwide research is focused on obtaining an understanding of protein pathways in organisms, and on the correlation between protein modification and disease. Current thinking in biology avers that manifestation of disease states ultimately involves the interaction of proteins in a manner that differs from non-disease tissue. The interest in understanding protein function is therefore becoming prevalent in all biologically relevant fields, including proteomics, biotechnology, drug discovery, and molecular diagnostics.

The study of protein samples obtained directly from tissue or cell media or cell media is extremely difficult work. Many biologically significant proteins are present in minute quantities in living organisms, and can be produced using in vitro methods only in limited and minute quantities.

One conventional technique for protein identification is mass spectrometry (MS) as a detection and quantification tool. Mass spectrometry is often used because it is more or less universally amenable to diverse analytes, and provides large amounts of useful analytical information from relatively small amounts of biological sample.

Mass spectrometry is conventionally used in biological research and development activities to identify unknown compounds, or to examine the structure or abundance of certain compounds. Simply put, a mass spectrometer is a detector that is capable of identifying the molecular mass of constituents within a mixture. The mass spectrometer produces a mass spectrum that can be used to identify unknowns or to determine the basic building blocks that constitute a molecule's structure.

Conventional MS identification techniques typically rely on four steps:

1) The analyte (e.g. protein or peptide) is separated from its complex biological matrix and converted to an analyzable species. Typical methods used in this step may involve any combination of such techniques as gel electrophoresis, adsorption chromatography, size exclusion chromatography, immunoprecipitation, blotting, osmosis, and chemical labeling, amongst many others. The methodology chosen for a given application typically depends on the nature of the analyte, its matrix, and the type of information required from the investigation.

2) The sample is ionized to produce gas-phase molecular ions. The ionization method may be electrospray, nanospray, atmospheric pressure chemical ionization (APCI), or matrix assisted laser desorption/ionization (MALDI), amongst others. In conventional methods, electrospray, nanospray, and MALDI are utilized for the analysis of proteins and peptides.

3) The analyte's molecular ion is introduced into a high vacuum and fragmented to produce ions. The number and size of the "daughter" ions produced are determined by the structure of the analyte and the fragmentation method. Typically, molecular ions are fragmented inside the mass spectrometer by colliding with them with a low-pressure gas.

4) The molecular fragments are sorted according to molecular mass and detected, producing a fingerprint of the original protein. This fingerprint can be used to determine characteristics (e.g., identity, quantity, or structure) of the unknown protein.

The methods used in step 1 are also conventional in most other fields of biological and chemical analysis and are not limited in scope to MS detection methods.

For complex and more difficult protein separation and analysis, the ionization procedure in step 2 often employs nanospray techniques. The reasons for this method choice may include: 1) very small sample volumes typically require low flow rate analytical methods for efficient analysis, 2) the nanospray procedure is typically amenable to established chromatographic methods (albeit at lower flow rates), and 3) the efficiency of sample ionization increases with reduction in flow rate (thus increasing the sensitivity of analysis for low-abundance proteins/peptides).

In conventional nanospray applications, an analyte flow stream is ionized and introduced into a mass spectrometer by passing a solution of the analyte through a very small (e.g., about 20 µm inner diameter) high voltage electrified needle. The fluid passing through the needle accepts electrical charge imparted by the applied voltage, and emerges from the open end of the capillary as a finely dispersed aerosol. This charged aerosol travels at atmospheric pressure toward a counter electrode at the mass spectrometer entrance. Once the aerosol enters the mass spectrometer, it largely consists of gas-phase ions that may be analyzed using steps 3 and 4 above. Such nanospray methods require flow rates in the range of 10-1,000 nl/min, which is much lower than flow provided by conventional chromatographic methods.

In addition to mass spectrometric elucidation methods, diagnostic research has been increasingly concerned with investigating biological systems using microelectromechanical systems (MEMS). When applied to biological investigation, these methods are sometimes referred to as Lab-on-a-chip (LOC) analyses. Systemically, many LOC instruments can be viewed as incorporating nano flow, microarray, and biosensor technologies into an integrated device. In a typical approach, macroscopic analytical devices (e.g., valves, columns, detection chambers, and flow channels) are miniaturized and micro-fabricated onto glass, silicon, or polymeric material.

To date, such systems and methods utilize non-feedback based pumping solutions, including syringe and positive displacement pumps. Because of the relatively small flow rates required in such applications, many conventional systems utilize electroosmotic flow (EOF) pumping in lieu of mechanical pumps. Although the EOF pumping method is convenient to use and can operate at low average flow rates, it presents significant disadvantages when required for precise control, or when used on fluids that have high ionic strength.

In addition to the foregoing applications, worldwide experience over the past several years have heightened interest in the detection and elucidation of chemical or biological threat agents introduced into the environment through terrorist or military action.

In a conventional implementation, a point detector for such threat agents operates as a self-contained analytical module that is capable of analyzing environmental samples and initiating an alarm if hazards are found to be present above a prescribed threshold concentration. Current developmental point detection technologies rely on such conventional techniques as enzyme linked immunosorbent assay (ELISA), polymerase chain reaction (PCR), surface plasmon resonance (SPR), cell cytometry, cell staining, immunoprecipitation, mass spectrometry, and native fluorescence, to name a few.

In order to adapt higher flow methods to nanospray, lab-on-a-chip, or other ultra-low flow methodology, two different approaches have been utilized. In the "split flow" method, a fraction of the analytical fluid is split from a conventional high-flow stream into a low-flow stream and the reduced flow stream is applied to the analytical method. Equipment designed to do this are known as splitflow instruments. In the typical conventional split flow configuration, the flow stream is passed into a tee connector with different backpressures generated on each outlet arm of the tee. One arm becomes the high-flow arm and the other becomes the low-flow arm. The ratio of high to low flow is determined by the pressure ratio between the two arms. Flow split ratio can be adjusted by changing tubing lengths or diameters (thus adjusting the pressure generated at a given flow rate) on each arm.

The two largest disadvantages of the split flow technique are that most of the analytical solvents is discarded in the process, and that high precision is very difficult (or impossible) to obtain at low flow rates. Imprecision in flow rates can easily result from changes in temperature, particulates in the fluid, or gradual changes in backpressure created from downstream devices.

In "splitless" methods, the chromatographic and upstream fluid systems are converted to low flow technologies. This method requires pumping and fluid transfer systems that are capable of operating at rates from 10-1,000 nl/min. Such methods are deemed splitless flow. The main disadvantages of this method are the requirements for precise control of ultra-low flow rates and the requirement for very low dead volume flow paths in the instrumentation. The splitless configuration has the advantage of very low solvent consumption, and is directly amenable to injection and handling of very small samples.

Analytical methods and systems have been developed that demand sensitive high-throughput analyses of biological materials in small quantities. Often, such analyses require precise control of the fluid flow rates in the range of about one (1) nano-liter (nL) per minute to about five (5) microliters (µL) per minute, with pressures varying over a range of several orders of magnitude. Such analytical applications include, among others, nano-scale liquid chromatography (nano-LC), mass spectrometry (MS), or capillary electrophoresis (CE). These microfluidic applications typically utilize fluid flow rates as low as tens of nanoliters per minute up to several microlitres per minute. Designing systems to precisely achieve and maintain ultra-low flow rates is a difficult task, fraught with several potential problems.

One problem affecting such microfluidic techniques comes from the susceptibility of various components of systems used for conventional ultra-low flow applications to compress or decompress in response to a change in system pressure. This component adjustment to pressure change often creates a significant delay time before achieving a desired flow rate in conventional microfluidic systems and applications, and can also hinder accurate flow rate adjustment in such systems and applications.

Another persistent problem with such conventional microfluidic systems and applications occurs when air or other gases are inadvertently entrained into the flow path of such a system. If these compressible gases are present in the flow path of conventional systems for such applications, the compression and expansion of gas bubbles creates difficulties in achieving a desired flow rate.

In many conventional microfluidic systems, the flow rate of a fluid is established in a pump by displacing liquid at a controlled rate using, for example, a piston or syringe plunger. To obtain desired flow rates in such conventional systems, the displacing element of the pump is moved at a fixed velocity using a preprogrammed control system. Such conventional systems often show undesirable flow rate fluctuations created from imprecision in the mechanical construction of the drive system used to displace the liquid. In conventional lead screw-driven systems, for example, inaccuracies often arise from periodic changes in screw characteristics as the screw turns through a complete revolution, and from inaccuracies in thread pitch along the screw, among other types of mechanical errors.

In order to overcome these difficulties in achieving and maintaining desired flow rates, conventional flow sensors may be employed to allow the system to compensate for inaccuracies through use of a feedback loop to a preprogrammed control system. Many conventional flow sensors used in microfluidic analysis, such as the SLG1430 sensor that is commercially available from Sensirion Inc. (of Zurich, Switzerland), have a non-linear response to fluid flow. For such flow sensors, the sensor response to increasing flow rate approximates a polynomial equation, with the equation order and constants dependent on variables such as flow sensor design, the liquid that is being monitored, and the operating flow rate range.

In order to use such conventional flow sensors to measure and maintain accurate ultra-low flow rates in conventional systems via a feedback loop, the sensor must be calibrated for the solvent that is to be passed through the sensor. Conventional calibration methods usually involve preparation of a list of the sensor responses at different flow rates for a given solvent. When a particular solvent is used, the actual flow rate is obtained by comparing the sensor response to tabulated calibration values gathered from repeated observations made for that particular sensor and solvent combination. Calibration curves for a given sensor and solvent can be obtained by fitting the calibration data to a best-fit curve from the empirical data in such conventional calibration methods.

A major problem with this conventional calibration tabular methodology is that data values must be collected for any solution mixture that is to be passed through the system. Doing so for numerous solvents can require a significant amount of time and effort. Moreover, for reliable operation, this data must be collected using a precise flow rate reference. Often, a conventional microfluidic system will be used to deliver different solutions that possess diverse characteristics, and calibrating a conventional system for these various solutions is often time consuming and laborious.

In conventional chromatograph applications, analytical columns consist of narrow-bore tubes made of fused silica, polymeric material, stainless steel, or other material that should be compatible with the analyte mixture and mobile phase. The columns may be one centimeter to several meters long, and they are typically packed with small beads ranging in size from a few microns to several millimeters in diameter. The tubes may have fritted on the downstream end to prevent loss of beads when liquid is flowed through. Long-chain carbon polymers are coated on the beads to comprise the stationary phase in conventional reverse-phase separations. A sample is introduced into the head of the column using an injection valve. Detection is performed using UV absorbance, fluorescence, mass spectrometry, emission spectroscopy, nuclear magnetic resonance (NMR), or some other method that is sensitive to the analyte in question.

When the analyte compounds are similar in nature, then the mobile phase mixture can remain constant throughout the entire separation. This type of separation is known as isocratic. For more complex mixtures that contain diverse compounds covering a range of hydrophobicity, increasing the organic content of the mobile phase during the separation may be desired. This later method is known as gradient chromatography.

In a conventional reverse-phase gradient chromatography analysis, the amount of organic modifier in the mobile phase may be increased from the beginning of the analysis until elution of the most hydrophobic compounds. This increase in hydrophobic nature of the mobile phase serves to enhance elution of very highly retained compounds, but allows the weakly-retained compounds to separate under low organic modifier concentrations.

SUMMARY OF THE INVENTION

The present invention, among other things, provides a method for calibrating a liquid flow sensor by pumping a volume of a fluid through the sensor for a series of fixed rates. In one embodiment, the flow rate is first determined by moving a displacing element at a controlled velocity and, by use of a valve, allowing the system output to dispense through a low-pressure orifice or piece of tubing. Because the system is pumping at low pressure during the calibration procedure, system response is rapid, regardless of component compressibility or entrapped gas pockets. In fluidic systems that utilize lead screw drives, flow sensor response is determined by averaging the measured flow rate for a complete revolution of the pump lead screw, thereby minimizing periodic lead screw derived flow rate noise.

The flow sensor response can be determined for several different flow rates, depending on the order of polynomial fit. In one embodiment, the sensor response is approximated using the general equation:

$$y = ax^2 + bx + c$$

where y is the sensor response, x is the actual flow rate, a is the first quadratic constant, b is the second quadratic constant, and c is the equation intercept, which is the sensor response measured with no fluid flow. In this embodiment, the constants can be determined by measuring the sensor response and actual flow rate at three individual pump infusion rates.

In another embodiment, during which a flow sensor can be calibrated during operation of an analytical system, the actual flow rate is determined by evaluating the quadratic equation using:

$$x = \frac{-b \pm \sqrt{b^2 - 4ac}}{2a}$$

using the real root. In this embodiment, x is determined from the measured flow sensor response.

In yet another embodiment, the sensor may be calibrated in the same general way over a larger flow rate range by extending the order of the polynomial and using more calibration data points to determine the constants.

In another embodiment, a gradient flow system with two or more pumps with corresponding drivers, fluid sources, selection valves, and flow sensors may be used to mix fluids from the two or more sources. In such a system, one or more of the pumps may be calibrated as summarized above and described below. In addition, and in another embodiment, controllers may be used in such a gradient system so that one or more pumps is automatically calibrated. In addition, the flow rate of one or more of the fluids in a gradient system may be controlled automatically in response to signals from one or more flow sensors in the gradient system.

It is an object of the invention to provide methods and apparatus which allow precise calibration of a flow sensor in a system which has periodic flow rate fluctuations.

It is another object of the invention to provide methods and apparatus which allow precise calibration of a flow sensor by minimizing the potential effects of trapped gases or compression of system components.

It is yet another object of the invention to provide methods and apparatus which allows precise calibration of a flow sensor for use with a given fluid over a wide range of flow rates.

It is yet another object of the invention to provide methods and apparatus to allow precise calibration of a flow sensor during operation of an analytical system to thereby allow an operator to obtain a desired flow rate.

It is an object of the invention to provide a method that accurately and precisely allows an operator to calibrate a flow sensor for a particular fluid more quickly and easily than conventional methods.

It is an object of the invention to provide a method which allows an operator to calibrate a flow sensor for a fluid without having to generate or use a table of empirical data.

It is an object of the invention to provide a method that allows precise flow control using inexpensive, mechanically-driven pump systems.

It is an object of the invention to provide a method that allows rapid in-situ calibration of a flow sensor while consuming small amounts of fluid.

These and other objects and advantages of the invention will be apparent from the following detailed description.

DETAILED DESCRIPTION OF THE DRAWINGS

FIGS. 7A-7S are examples of source code in accordance with the present invention.

FIG. 12 is a diagram illustration flow rates obtained with a system in accordance with the present invention.

FIG. 13 is a diagram illustrating flow responses obtained with a system in accordance with the present invention.

FIG. 14 is a diagram illustrating a designed step change in flow rate obtained with a system in accordance with the present invention.

DETAILED DESCRIPTION OF THE PREFERRED EMBODIMENT

Figure 1:
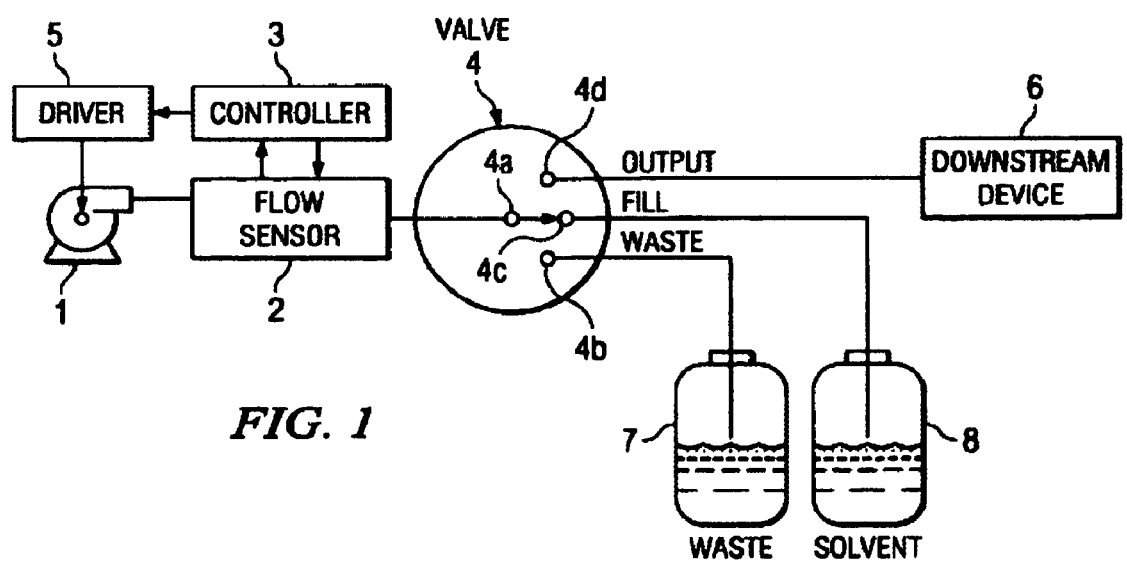
FIG. 1 is a schematic diagram of the components of a fluidic system in accordance with the present invention.

Referring to FIG. 1, the components of a fluid control system are depicted. It will be appreciated by those skilled in the art that the methods and apparatus of the invention may be used with chromatography, mass spectrometry, capillary electrophoresis, or other analytical applications and systems. As shown in FIG. 1, this particular embodiment of the fluid control system includes a selection valve 4 with a plurality of ports. One port 4a of valve 4 has a fluid connection to a first side of flow sensor 2. The second side of flow sensor 2 has a fluid connection to the input and output port of a pump 1. Those skilled in the art will appreciate that any one of a number of conventional selection valves, flow sensors, and pumps may be used for valve 4, sensor 2, and pump 1. For best results, I prefer to use the 100 μl positive displacement pump which is commercially available from Sapphire Engineering Inc. (Pocasset, Mass., USA), the flow sensor SLG 1430 which is commercially available from Sensirion Inc. (Zurich, Switzerland), and the V-485 selection valve that is commercially available from Upchurch Scientific, Inc. (Oak Harbor, Wash., USA).

As shown in FIG. 1, the pump 1 is electronically connected to a controller 3 which, in turn, is electronically connected to a driver 5. The controller 3 is also electronically connected to the sensor 2. The controller 3 can be preprogrammed with computer software to perform the steps of the method of the invention. For best results, I prefer to use as the driver 5, a driver MICROLYNX® which is commercially available from Intelligent Motion Systems Inc. (of Marlborough, Conn., USA). The controller 3 preferably consists of a preprogrammed PIC 18F452 microcontroller, which is commercially available from Microchip Technologies Inc. (of Chandler, Ariz., USA) with serial communications and digital input/output connections. The controller 3 is essentially an application specific integrated circuit, with the computer program incorporated therein. The computer program preferably is written to allow the controller 3 and the system to perform the steps detailed below.

Still referring to FIG. 1, it can be seen that at least one of the output ports of valve 4 is in fluid communication with a waste receptacle 7. Another port of the valve 4 is in fluid communication with a reservoir 8, which holds the subject fluid to be considered for purposes of calibration (often referred to as the solvent). The port 4d of the valve 4 is in fluid connection with the input of a downstream analytical system 6. Those skilled in the art will appreciate that any of a number of analytical systems may represent the downstream analytical system, including chromatography or mass spectrometry systems.

The controller 3 is electronically connected to the valve 4, and controls the position of the valve 4. Those skilled in the art will appreciate that any of a number of analytical systems or devices may be attached to other unused ports on the chosen selection valve.

Figure 2:
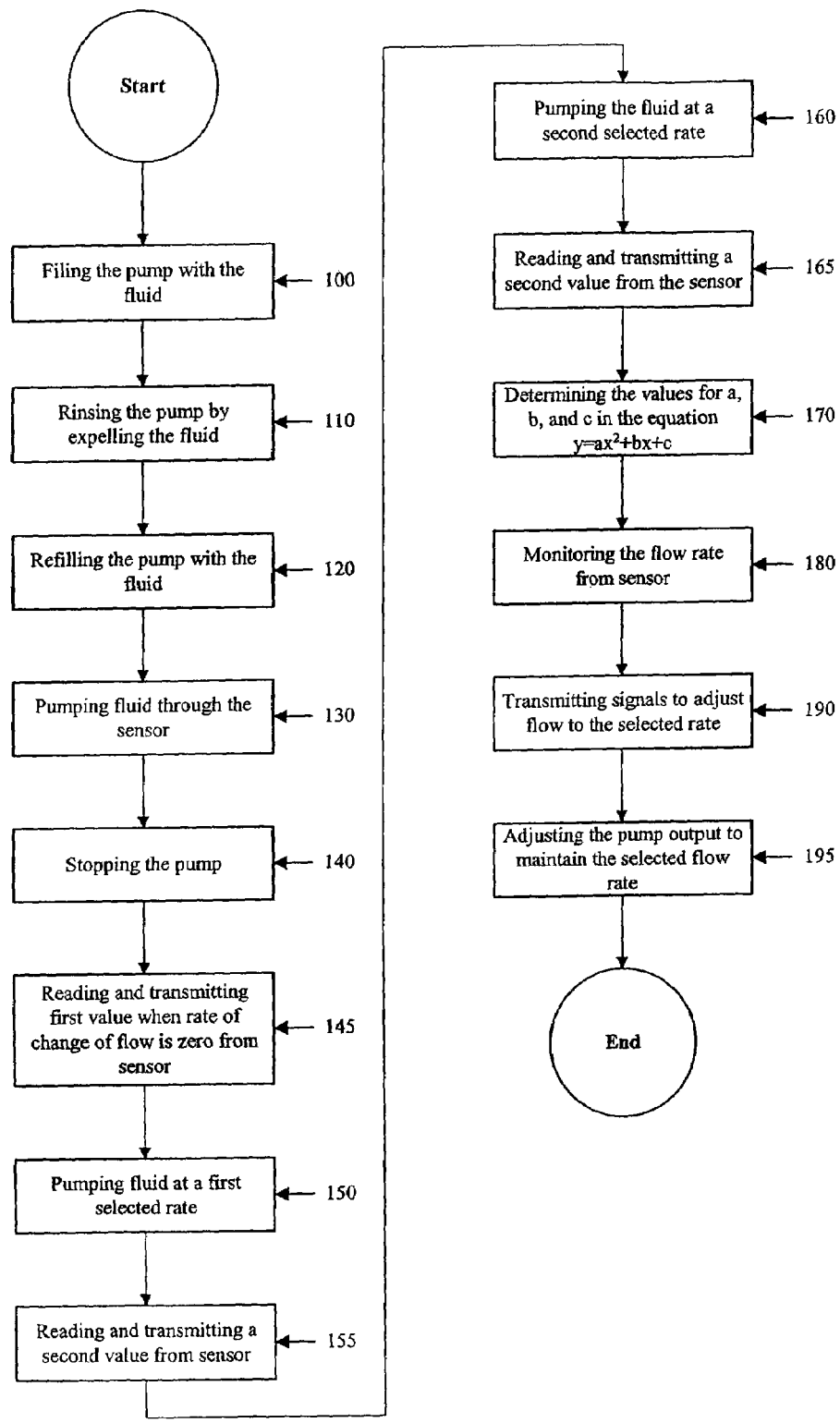
FIG. 2 is a flow diagram showing the steps of a method in accordance with the present invention.

Referring now to FIG. 2, the steps of the method of the invention will be described with respect to the flow diagram. (For ease of reference, the same numbers are used to refer to the components shown in FIG. 1.) Before beginning the calibration cycle, it is useful to first purge and prime the system to remove excess trapped air or other gases. Accordingly, step 100 is filling the pump 1 (in FIG. 1) from the reservoir 8 via the selection valve 4. Next, the pump 1 is rinsed 110 by expelling the fluid in the pump 1 to a waste receptacle via valve 4. The pump 1 is then refilled 120 with the fluid of interest. Together, steps 100, 110, and 120 can be considered the purging/priming cycle.

Still referring to FIG. 2, the calibration cycle is described next. In step 130, an operator pumps a volume of the fluid through the sensor 2 to a waste receptacle via the valve 4. There will be negligible pressure present in the system during this step 130. The operator then stops the pump 1 and the flow of the fluid through the sensor 2 at step 140. Once the rate of change of flow sensed by the sensor 2 has minimized, the flow sensor will output this value and transmit it to the controller 3 as step 145. This value transmitted to the controller 3 at step 145 will be considered the constant c in the equation $y=ax^2+bx+c$ in the quadratic equation (or, if the controller is programmed to solve a cubic or other equation, the value shall be deemed the constant in such equation corresponding to the y-intercept in the equation).

During the next step 150, the operator then starts the pump 1 to pump the fluid so that it flows at a preselected rate, such as 2 microliters per minute through the sensor 2 and to a waste receptacle. The rate of flow can be determined by knowing the linear distance that the piston of the pump 1 travels based on the pitch of the lead screw thread that drives the piston of the pump 1. The cross-sectional area of the piston in pump 1 is also known. Thus, the volume of the fluid moved per unit time per rotation of the lead screw (or the lead screw nut, as the case may be) is known or readily determined. For best results, the calibration step 150 should be performed only with the output of the fluid flowing to waste so that there is negligible back pressure within the microfluidic system and therefore any elasticity of any components within the system will not be of significance in the calibration. Once the preselected first flow rate is reached, the sensor 2 will transmit a second averaged value to the controller 3 at step 155. This averaged value is determined by averaging the flow sensor response for the entire cycle of periodic noise in the pump mechanism. In the case of a lead screw driven pump, the flow rate is averaged for a complete turn of the lead screw.

Still referring to FIG. 2, the operator then sets the pump 1 to pump the fluid so that it flows at a second preselected rate at step 160, such as 4 microliters per minute, through the sensor 2 and to a waste receptacle. As noted above, the rate of flow can be determined precisely by knowing the dimensions of the distance traveled by the lead screw of the piston of pump 1 and the area of the piston in pump 1. In step 165, once the second preselected flow rate is reached, the sensor 2 will transmit a third value to the controller 3. This averaged value is determined by averaging the flow sensor response for the entire cycle of periodic noise in the pump mechanism. In the case of a lead screw driven pump, the flow rate is averaged for a complete turn of the lead screw.

For the highest order n in the equation to be solved, we prefer to measure and determine the sensor 2 responses for n+1 different flow rates. By using the measured flow sensor 2 responses and the known pumping rate of the fluid for the corresponding sensor 2 output responses, the operator can determine at step 170 the constants a, b, and c for the quadratic equation (and other constants where the equation to be used has higher orders than the second). Alternatively, the controller 3 can be preprogrammed to determine 170 the values of the constants.

Once the sensor 2 has been calibrated in accordance with the invention, the system can be used by the operator as follows: The operator can for example read the output of the flow sensor 2 during operation of the system at step 180. The flow rate value output by the sensor 2 can also be determined automatically by the preprogrammed controller 3. The controller 3 can be preprogrammed so that it transmits appropriate signals to driver 5 at step 190 depending on the incremental values of flow rate of change measured by the sensor 2 and transmitted to the controller 3. The driver 5 then adjusts the output of the pump 1 based on the signals received by sensor 2 to maintain the flow rate set by the operator of the system at step 195.

Although not shown (apart from controller 3), those skilled in the art will appreciate that a preprogrammed computer can be used as the controller 3. Those skilled in the art will appreciate that such a computer can be easily programmed to receive and store the values it receives from the sensor 2, together with the information for determining the flow rate based on the dimensions of the pump. The programmed computer can be set so that it automatically calculates the constants a, b, and c (or others depending on the particular equation to be solved) and then outputs those values for use by the operator. Similarly, the computer (not shown apart from controller 3) can be preprogrammed with such constants so that the computer receives updated signals corresponding to the flow rate as determined by the sensor 2 during operation, the computer (not shown apart from controller 3) and, as appropriate according to its programmed instructions, sends signals to the driver 5 to adjust the pump 1 to obtain the flow rate selected by the operator for operation of the system 1. Those skilled in the art will appreciate that such computer programs can be stored on the hard drive of the computer (not shown apart from controller 3), or on a disk, CDROM, DVD, EEPROM, ASIC, per drive, or other electronic storage device with non-volatile memory.

Figure 3:
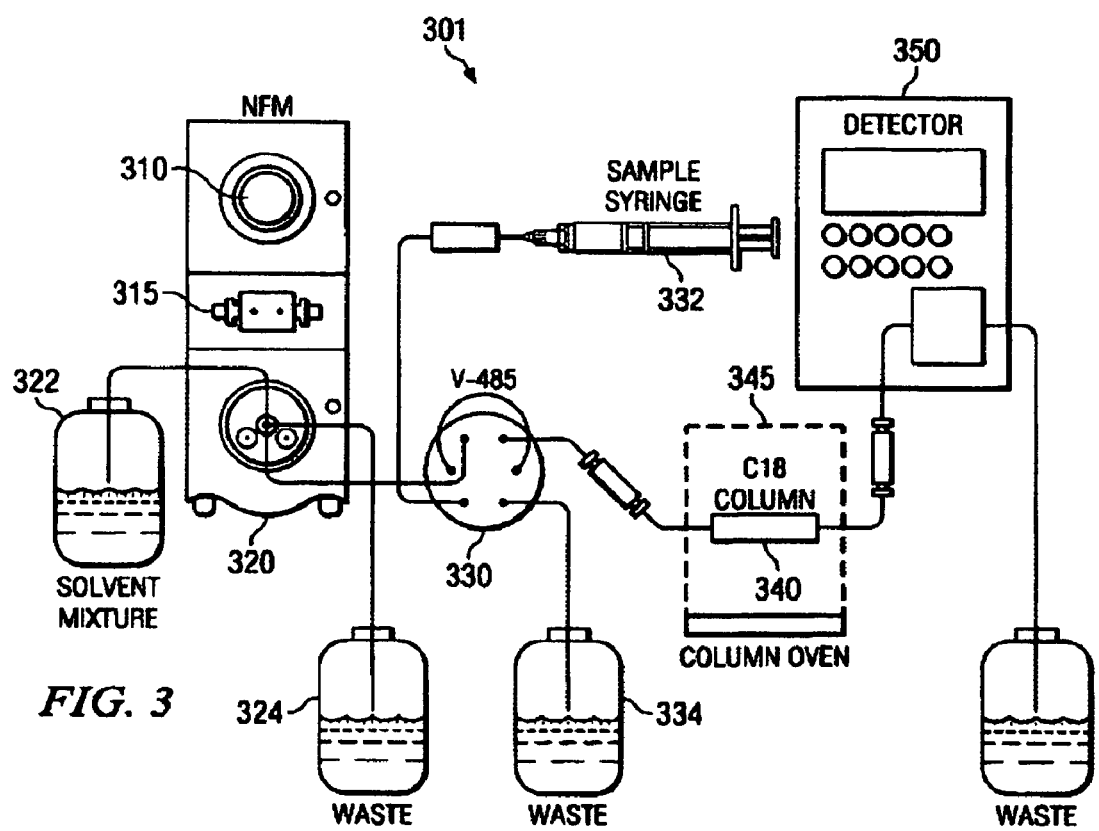
FIG. 3 is a schematic diagram of a system used to provide an example test of the methods of the present invention.

Referring now to FIG. 3, an experimental system 301 used to evaluate one embodiment of the invention is shown. In FIG. 3, the system 301 includes a high-pressure positive displacement pump 310, an inline non-invasive flow sensor 315, and a four-way selection valve 320 (for filling and dispensing solvent mixtures in the system 301). The system 301 maintains a precise flow rate to a desired value regardless of back pressure in system 301. The system 301 is able to use the output signal from the flow sensor 315 to adjust the piston velocity of the pump 310 to clamp the output flow rate from the pump 310 to the selected value. As shown in FIG. 3, the experimental system 301 also includes a source of a solvent 322, which is in fluid communication with the flow sensor 315. The flow sensor 315, in turn, is connected to allow fluid communication with both a waste receptacle 324 and an injection valve 330. The injection valve is also in fluid communication with a sample syringe 332 and a second waste receptacle 334. In addition, the injection valve 330 is in fluid communication with a first end of a column 340, which is housed within a column oven 345. The column oven 345 is used to maintain the temperature of the column 340 at 35.0° C.±0.05° C. The second end of the column 340 is in fluid communication with a detector 350. For this experiment, I used a V-485 NANOPEAK injection valve (commercially available from Upchurch Scientific of Oak Harbor, Wash.) for the injection valve 330, a 15 cm by 75 µm inner diameter nano column (the PEPMAP C18 column commercially available from LC Packings of Amsterdam, The Netherlands) for the column 340, and an ULTIMATE UV detector (also commercially available from LC Packings of Amsterdam, The Netherlands) for the detector 350.

Figure 4:
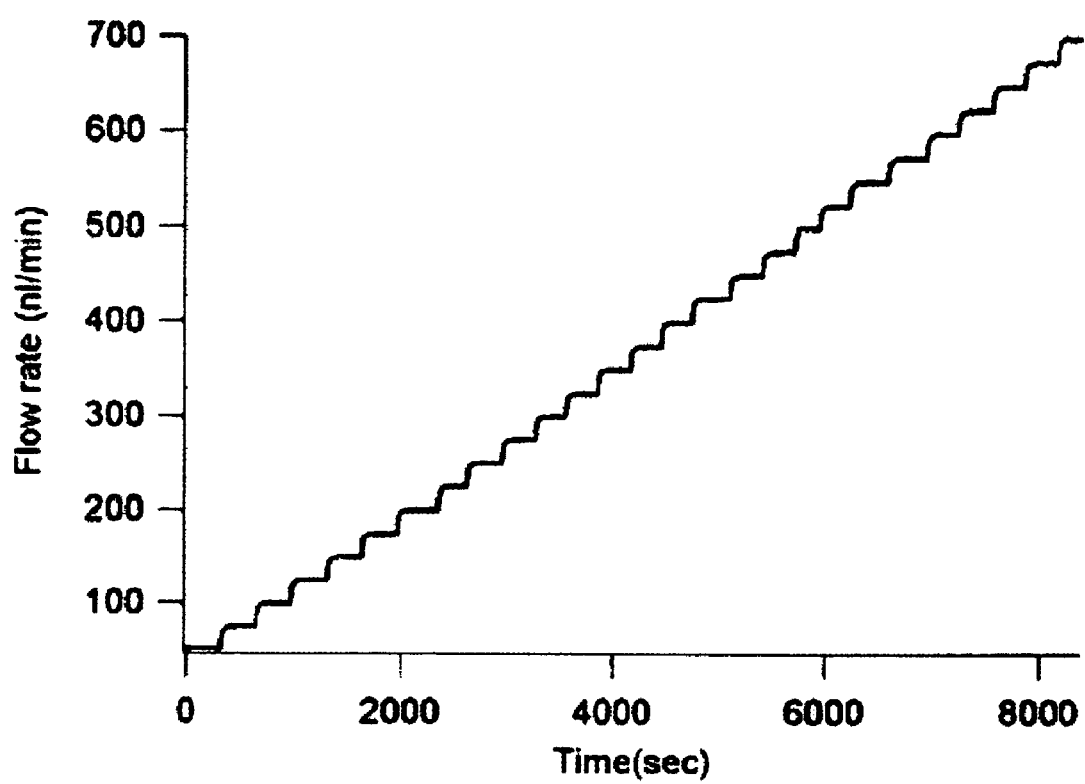
FIG. 4 is a graph showing the data collected in one example of the present invention.

Using a timed injection routine, numerous 5 nL plugs of a mixture consisting of naphthalene, fluorine, biphenyl, and uracil dissolved in 75% acetonitrile/water were repeatedly injected into the column 340. Analytes were detected via absorbance at 250 nm using the detector 350. All experimental data were collected at 1.6 Hz using analog/digital circuitry and preprogrammed computer software performing the methods described above. The data collected are shown graphically in FIG. 4. As shown in FIG. 4, the system flow sensor output for a variety of increasing flow rates applied to the column 340 (over a range of 50 nL/minute to 700 nL/minute) shows that the system flow sensor possesses a 90% risetime of 12 seconds at 700 nL/minute (a pressure of 3,000 psi) and exhibits a RMS flow rate noise of approximately 1 nL/minute at an output flow rate of 50 nL/minute.

Figure 5:
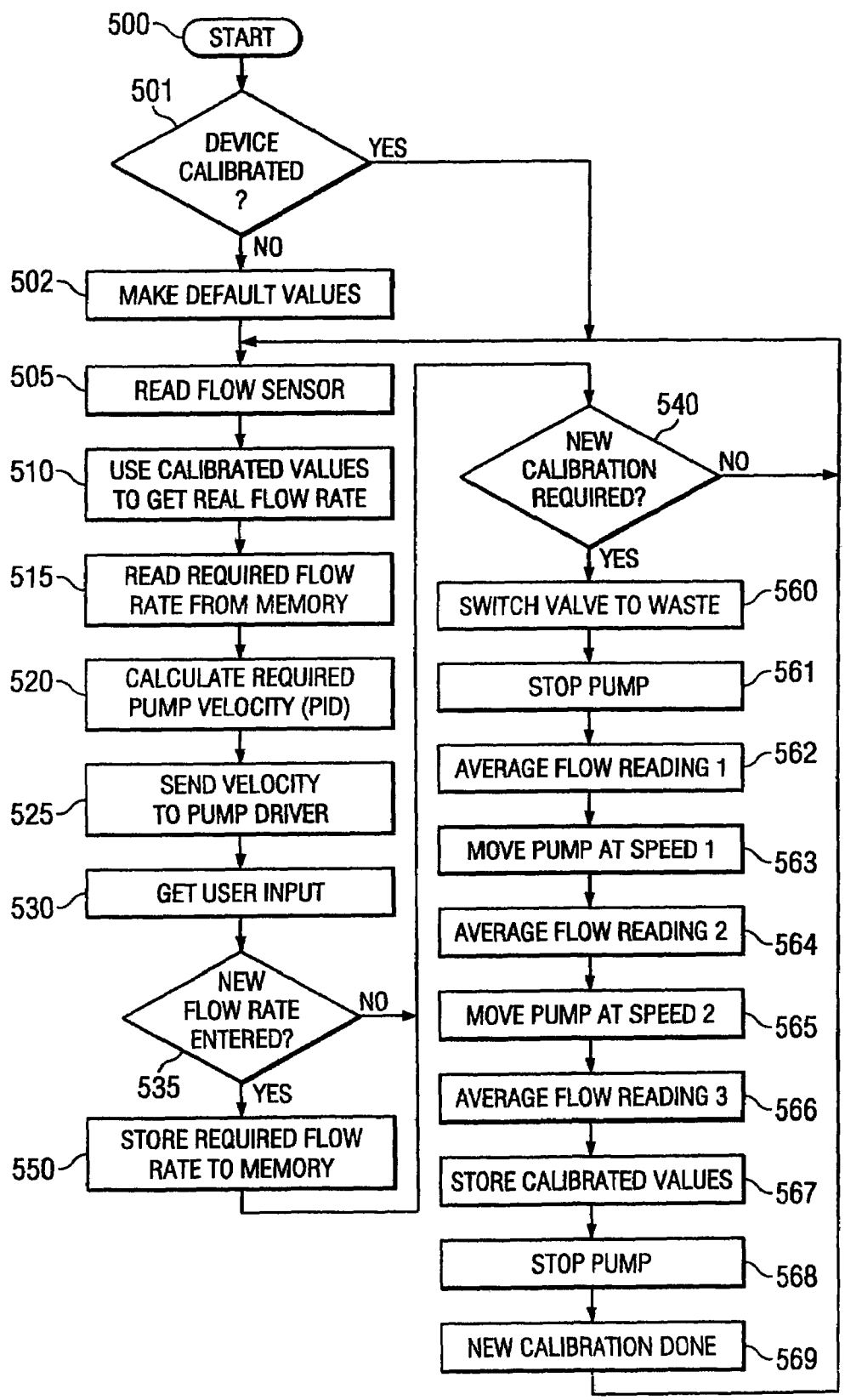
FIG. 5 is a flow diagram showing an alternative embodiment of the present invention.

Referring now to FIG. 5, a flow chart of an another alternative embodiment of the present invention is shown. In step 500, the system begins the methods of the invention. In step 501, the system checks to see if the flow sensor has already been calibrated. This can be done by checking a flag or the status of a value stored in computer memory. If the flow sensor has been determined to have been calibrated at step 501, then the next step is reading the data value from the flow sensor at step 505. This step 505 is repeated as many times as is necessary to obtain the data values needed to calculate the constants for the polynomial equation to be solved. If the equation is of the order n, then at least n+1 data values should be measured. For example, if the flow sensor is known to have a non-linear response that is quadratic, then the program will need to measure at least three data values in order to solve the equation $y=ax^2+bx+c$. Similarly, if the equation used to model the response of the flow sensor is cubic, then at least four data values should be read from the flow sensor.

Still referring to FIG. 5, the data values read in step 505 are provided to the preprogrammed computer (not shown in FIG. 5) so that it can use the data values measured by the flow sensor to calculate the constants and solve the polynomial equation. By solving the equation, the computer has calculated a value for the real flow rate of the system at step 510. Next, at step 515, the computer reads the required flow rate from memory. This value can be input by the operator when setting up the system. At step 520, the computer then calculates the required pump velocity needed to achieve the preselected flow rate based on the value of the real flow rate and the stored value for the desired flow rate. At step 525, the computer then sends a signal to the pump driver in order to have the pump operate at the required velocity determined in step 520. At step 530, the system checks to see if the user or operator has input a new flow rate. If not, the next step is to determine if a new calibration is required. Of course, an operator may choose to calibrate based on the passage of time or after some other selected interval or event has occurred. If not, the next step is to repeat step 505 and continue the foregoing cycle. If a user has input a new flow rate, the system first stores the new value in computer memory at step 550, as shown in FIG. 5. The system then checks to see whether a new calibration is required at step 540.

Still referring to FIG. 5, if the computer determines that a new calibration is needed at step 540, the computer then performs the following steps. First, the computer sends a signal to the valve (not shown in FIG. 5) to switch the fluid communication with at least one valve port to a waste receptacle at step 560. Next, at step 561, the computer sends a signal to stop the pump. At step 562, the data value is read from the flow sensor. Although this can be a single data reading, I prefer to have a number of readings taken of the flow sensor's reading, each of which can be stored in the computer memory and then averaged. Once the average has been obtained in step 562, the computer sends a signal to have the pump operate at a preselected first speed at step 563. In step 564, a number of values are read from the flow sensor, stored in computer memory and an average of those values is determined. Next, in step 565, the computer sends a signal to the pump to have it operated at a second preselected speed. In step 566, a number of readings are taken of the flow sensor, stored in computer memory, and an average is determined. In step 567, the computer stores the values for the averages determined in the steps 562, 564, and 566 in computer memory. At step 568, the computer then sends a signal to stop the pump. The computer then calculates the constants for the polynomial equation corresponding to the flow sensor using a least-squares algorithm (sometimes referred to as a "best square fit"), or a similar algorithm. Once the constants have been calculated and the equation solved, the computer can use those values in the equation based on the new required flow rate input and the new calibration is completed at step 569. Once the new calibration is completed at step 569, the computer can then repeat the performance of the steps by returning to step 505 and reading the values of the flow rate from the flow sensor.

Figure 6:
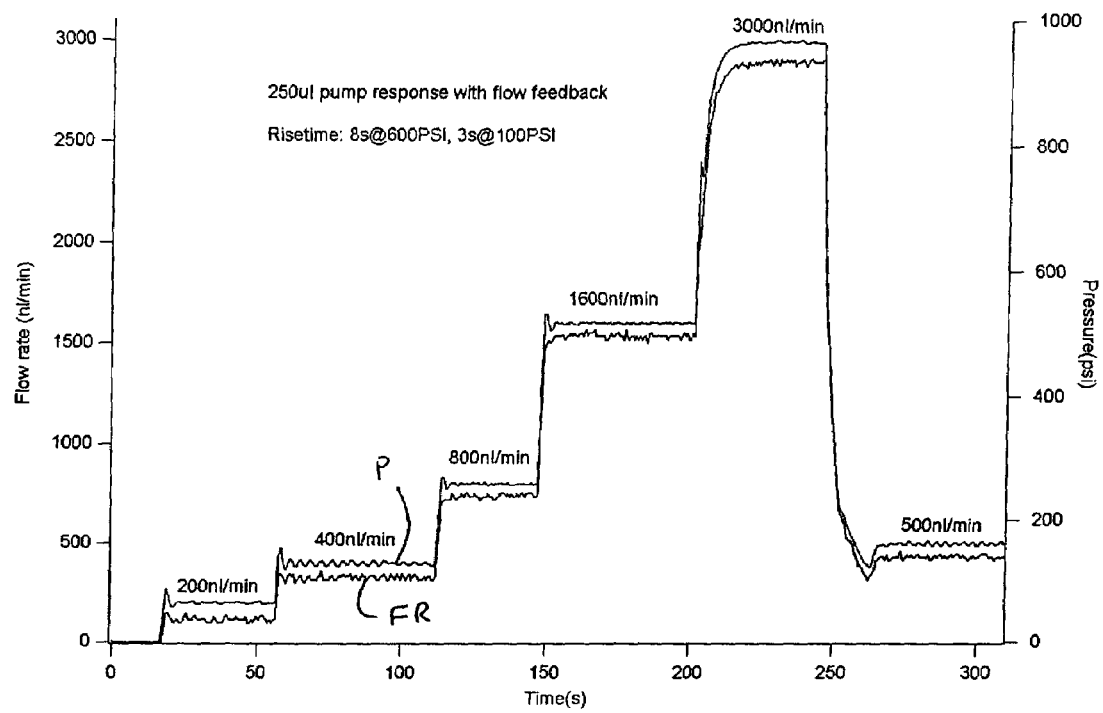
FIG. 6 is a graph showing data collected in another example of the present invention.

Referring now to FIG. 6, data from another example of the present invention is provided in graphical form. In FIG. 6, the flow rate FR is shown, as is the measured pressure P. FIG. 6 shows that the pressure P rapidly adjusts to changes made to the flow rate in a system using the methods of the present invention.

Now referring to FIGS. 7A-7S, source code of a computer program is provided, in accordance with one embodiment of the present invention. The source code shown in FIGS. 7A-7S may be used to implement some or all of the steps of the methods of the present invention as described above.

Those skilled in the art will appreciate that the methods of the invention can be used to attenuate noise from mechanical sources, such as the leadscrew of the pump. This can be done by averaging the values obtained from the flow sensor over one entire rotation of the leadscrew. For example, when a stepping motor (not shown) is used to actuate the pump, the number of steps corresponding to a complete rotation of the leadscrew can be determined. For example, in the system used in the above example, the stepping motor (not shown) has 200 steps per complete revolution, and a complete revolution of the leadscrew pumps 5 μL of the fluid. At a rate of 1.56 Hz, the computer is able to obtain 94 data points per minute, all of which can be stored in memory of the computer and then averaged. This averaging eliminates the variations which can result from the mechanical variations in the leadscrew due to thread size and the like. Those skilled in the art will appreciate that this method can also be used to calibrate any mechanical pump that provides periodic noise (i.e., fluctuations in the data due to various mechanical features) by averaging the data values obtained over the entire period of the noise source, thus allowing a user to calibrate for noise from such pumps with drive mechanisms other than leadscrews.

Attached hereto as Appendix A, and incorporated fully by reference herein, is a copy of the User Guide—100 μL version for the Scivex Confluent Nano Fluidic Module. This Appendix A provides further details and information regarding the use of calibration methods and apparatus of the present invention, such as in the operation of a pump controlled by a preprogrammed computer which uses values measured by a flow sensor to calculate a solution to a polynomial equation, such as is described above, then uses the calculated values to determine what, if any, adjustments to the pump's actions need to be made to obtain a preselected flow rate.

Those skilled in the art will appreciate that the data points obtained using the methods of the invention can be used to perform other interpolation algorithms, such as a cubic spline. Such techniques include those described in the book "Numerical Recipes in C: The Art of Scientific Computing" by William H. Press, published by the Cambridge University Press in 1988, which is hereby incorporated by reference herein. Those of skill in the art will also appreciate that the methods of the invention can be used with other equipment and solution combinations. For example, a system using two pumps (not shown) and two solutions (not shown) that are mixed together using a T-junction (also not shown) can be used for a binary gradient system.

Figure 8:
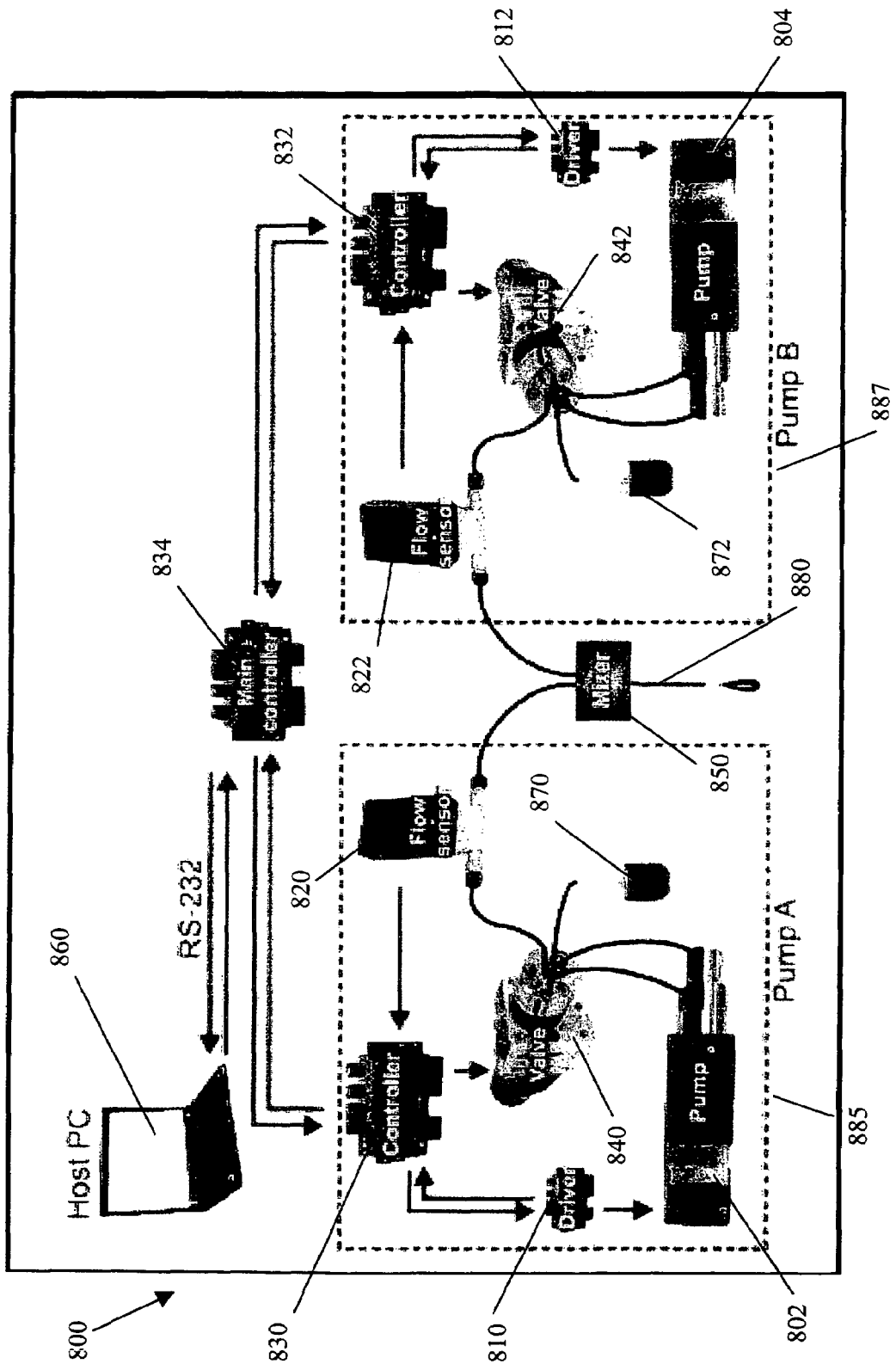
FIG. 8 is a schematic diagram of the components of a system in accordance with an embodiment of the present invention.

A new gradient system has been developed and an embodiment of the same is now described as follows. A new gradient nanoflow pump system 800 is designed to deliver splitless nano-gradients in the 50-4500 nanoliter per minute (nl/min) range, yet is able to operate at pressures as high as 5000 pounds per square inch or so. Moreover, it may be made of materials that are biocompatible and are otherwise compatible with most commonly used chromatography solvents. Referring now to FIG. 8, a schematic diagram of one embodiment of the gradient system 800 is shown. As shown in FIG. 8, gradient system 800 includes several components, including two high pressure positive displacement pumps 802, 804, two stepper motor drivers 810, 812, two in-line nano flow sensors 820, 822, three microcontrollers 830, 832, and 834, two actuated selection valves 840, 842, one mixing chamber 850, and a computer 860. In addition, FIG. 8 also shows the use of two fluid sources 870, 872. As shown in FIG. 8, the fluid sources 870, 872 are in fluid communication with at least one port of valves 840, 842, respectively. Outlet ports of valves 840, 842 are in turn in fluid communication with pumps 802, 804, respectively. Similarly, valves 840, 842 are in fluid communication with flow sensors 820, 822, respectively, which are in turn in fluid communication with mixer 850. A fluid outlet tube 880 is provided from the mixer 850; the outlet tube 880 provides the mixed fluid from the gradient system 800. As also shown in FIG. 8, the computer 360 is in electrical communication, such as via the RS-232 electronic signal protocol, with a main controller 834. The main controller 834, in turn, is in electrical communication with each of controllers 830, 832. In turn, controllers 830, 832 are in electrical communication with drivers 810, 812, and also with flow sensors 820, 822 and valves 840, 842, respectively. As described below, the system 800 can be considered as comprising two independent units 885, 887, which can be operated and function in the manner described below.

Still referring to FIG. 8, the operation of the gradient system 800 is now described. In normal operation, each pump 802, 804 is filled (and fluid is dispensed) through use of a three-position selection valve 840, 842. These valves 840, 842 act like the check valves commonly found in conventional higher flow pumping systems. The operation of these valves 840, 842 during filling, dispensing, and rinsing is described below.

The gradient system 800 can be operated as two independent pump units 885, 887 whose outputs are combined via a mixing chamber 850. Each pump unit 885, 887 is managed by a microcontroller 830, 832 that operates the valve 840, 842 and pump driver 810, 812, respectively. A common host controller 834 is responsible for timing and gradient formation; this controller synchronizes the activities of both pumps 885, 887. Those skilled in the art will understand that controllers 830, 832, and 834 execute pre-programmed computer software, and have associated memory and non-volatile memory. Those skilled in the art will also understood that computer 860 can be used in place of controllers 830, 832, and/or 834. I prefer to use controllers 830, 832, and 834, however, so that gradient system 800 can be a physically and/or operationally stand-alone unit. Examples of computer software for various functions are described both above and below.

When operating in normal feedback mode, the velocity of each pump 802, 804 is independently controlled using the signal from a flow sensor 820, 822 that is inline with the outlet of the pump 802, 804, respectively (via valves 840, 842, respectively). The controller 830, 832 for each pump 802, 804 interprets the respective flow sensor 820, 822 output signal and performs proportional-integral-derivative (PID) control on the pump 802, 804. This control is achieved by sending command codes to a micro-stepping motor driver 810, 812, respectively. In operation, the pump 802, 804 pistons are moved forward and backward to clamp the flow rate of the fluid emerging from the pump 802, 804 to a desired rate.

During operation, the selection valve 840, 842 for each pump 802, 804 is utilized to fill the pump 802, 804 from the rear port, and dispense liquids out the front port of each of pumps 802, 804. This filling and dispensing is achieved through the use of a selection valve 840, 842 that contains a fill groove in the rotor (not shown).

During pump filling operation, the pump 802, 804 piston may be retracted while the valve 840, 842 allows liquid to pass from the solvent reservoir 870, 872 and into the rear pump 802, 804 port. During this action, the front pump 802, 804 port may be plugged at the valve 840, 842.

For regular dispensing operation, the valve 840, 842 may be rotated to allow liquid to pass out the front pump 802, 804 port through the valve 840, 842 rotor and out the dispense line, respectively. The rear pump 802, 804 port may be plugged at the valve 840, 842, respectively, and the pump 802, 804 piston may be moved forward during this operation.

Solvent may also be delivered to a waste receptacle (not shown) by rotating the valve 840, 842 through one more position. In this configuration, the rear pump 802, 804 port is again blocked and fluid travels out the front port through a line to waste (not shown). This mode is useful for priming, rinsing, and calibrating the pumps 840, 842. During normal operation, the dispense line of each of pump 802, 804 may be attached inline to a flow sensor 820, 822. This attachment has been omitted from the diagram to simplify the description.

Because the gradient system 800 contains two pumps 802, 804 (one for each solvent), pumping may be performed by filling each pump 802, 804 with liquid, followed by dispensing the pump 802, 804 contents in a single stroke. The gradient system 800 supports operation at 250 nl/min and can provide 1000 minutes of analysis time before the pump 802, 804 must be refilled. During operation, both pumps 802, 804 combine output to provide the total flow, so run times may be very long at low rates.

Continuous flow pumping schemes can be developed for the gradient system 800, such as by incorporating additional pumps and controllers (not shown). Those skilled in the art will readily understand that the gradient system 800 may be used with such additional components.

The gradient system 800 uses non-invasive flow sensors 820, 822 for measurement and feedback of flow rate data. These sensors 820, 822 operate by measuring the flow-induced modulation of heat transfer through the wall of fused silica capillary. Different solution mixtures may possess disparate thermal characteristics, requiring re-calibration of the flow sensor 820, 822 if it is to be used for alternative solutions. The calibration techniques and apparatus discussed above may be used to precisely calibrate and adjust flow rates through the pumps 802, 804 and gradient system 800. The flow sensors may be of a type and configuration as is shown in Dykas, et al., U.S. Pat. No. 7,021,134 B2, issued Apr. 4, 2006, which is hereby incorporated by reference herein. Those skilled in the art will appreciate that other flow sensing apparatus may be used if desired.

For example, the gradient system 800 calibration procedure can automatically collect integrated flow information at several different flow rates. In this procedure, the pump 802, 804 may be rotated at one of four set rates and the flow rate data collected at this rate may be averaged for a complete 360° turn of the pump 802, 804 leadscrew. This averaging eliminates the leadscrew-induced flow noise described above. The flow data may be collected while dispensing fluid through a low-pressure waste line. This low-pressure dispense action prevents inaccuracies caused by system compressibility.

The raw sensor data collected during the calibration procedure may be used to produce a best-fit equation defining sensor response over the feedback operating range of the pump 802, 804. During normal operation, the flow sensor response in nl/min may be determined by interpolating this best-fit curve with raw sensor data. The individual pump controllers 830, 832 handle the best-fit interpolation and the collection of sensor calibration data internally.

One specific embodiment of the automated calibration routine is described in the following table:

TABLE 1

| Step | Description |
| --- | --- |
| 1 | Switch valve to the Dispense position. |
| 2 | Dispense fluid for ½ minute at 2000 nl/min |
| 3 | Stop pump |
| 4 | Switch valve to the Waste position |
| 5 | Average the zero flow response for ½ minute |
| 6 | Switch valve to the Dispense position |
| 7 | Increase the pump speed to 4 microliters per minute. |
| 8 | Integrate the flow sensor response for 1 turn of the pump lead screw. |
| 9 | Increase the pump speed to 6 microliters per minute. |
| 10 | Integrate the flow sensor response for 1 turn of the pump lead screw. |
| 11 | Increase the pump speed to 8 microliters per minute. |
| 12 | Integrate the flow sensor response for 1 turn of the pump lead screw. |

TABLE 1-continued

| Step | Description |
|---|---|
| 13 | Stop the pump |
| 14 | Calculate cubic equation |

Using this method, each fluid may be uniquely defined using four numbers: these numbers are the equation coefficients a, b, c, and d in the generic cubic equation $y=ax^3+bx^2+cx+d$. Users can upload and download the calibration equation for any solvent on each pump 802, 804. This functionality allows users to develop software that can store calibration information for a variety of commonly used solutions. For example, the values for constants a, b, c, and d can be determined for a given solvent or fluid and then stored in non-volatile memory of computer 860 or non-volatile memory of any or all of controllers 830, 832, 834. When a user wishes to begin later operations using the same solvent the operator can retrieve the values for constants a, b, c, and d from memory. Alternatively, the software can be pre-programmed so that the stored values for constants a, b, c, and d are retrieved automatically from memory in response to the user's input of solvent-identifying information and then used to calibrate the corresponding pump. Those skilled in the art will understand that such memory can be used to store values for various constants for various equations for various solvents, depending on the user's preferences. Those skilled in the art will also appreciate that values for such constants can be stored in association with the specific pump from which such values were determined.

In one embodiment, the gradient system 800 can be operated in three different modes: 1) direct control from a host computer 860, 2) stand-alone programmed operation, and 3) operation from digital signals presented to the system 800 (so-called contact closure control). All three of these control modes may be utilized in a given experiment. For example, a user may begin by homing and filling the pumps 802, 804 using direct commands from a host PC 860, and then the user downloads an automated gradient software program (not shown) to the system 800. After the gradient program has begun running on the system 800, it is usually timed and coordinated with data collection using contact closure control.

Figure 9:
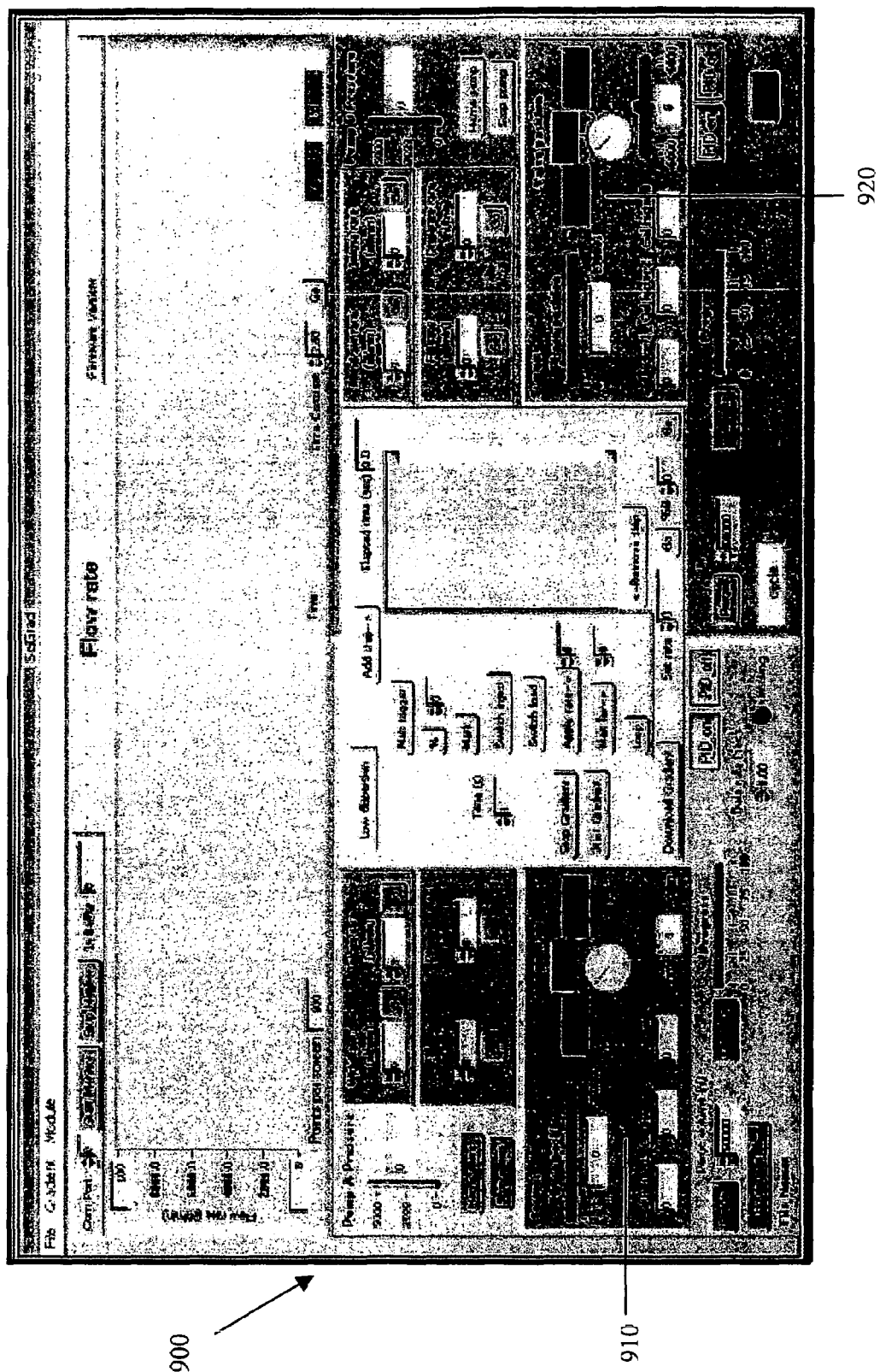
FIG. 9 is a graphic user interface provided to a user of a system in accordance with an embodiment of the present invention.

The gradient system 800 can be operated from a host computer 860 using a pre-defined command set communicated through RS-232 protocol. In one embodiment, a graphical user interface (GUI) may be used by an operator for operation and programming of the gradient system 800. The GUI 900 of one embodiment is shown in FIG. 9. As shown in FIG. 9, GUI 900 has a blue-tinted portion 910, with the blue portion 910 corresponding to the unit 885 (pump A) shown in FIG. 8, and red portion 920 corresponding to unit 887 (pump B) shown in FIG. 8. The data illustrated in red in FIG. 12 below corresponds to data from pump A 885, while the data illustrated in blue in FIG. 12 below corresponds to data from pump B 887. Those skilled in the art will appreciate that computer 860 may be of any desired type of conventional personal computer (PC), such as are commercially available from Dell Computer Corp. of Austin, Tex.

In one embodiment, the commands used for operating the gradient system 800 from a host PC 860 are given in Table 2. As evidenced by examining the table, the system 800 module provides diverse functionality, allowing the system 800 to be in a variety of modes (isocratic, gradient, load and wash, etc.). Each of the command may be sent to the system 800 using RS-232 protocol and is terminated with a carriage or simplicity of communication.

TABLE 2

| Command | Action |
|---|---|
| @axxxxxx | Set position of pump A to xxxxxx |
| @bxxxxxx | Set position of pump B to xxxxxx |
| oaxxx | Set pressure sensor offset of pump A (for pressure calibration) |
| obxxx | Set pressure sensor offset of pump B (for pressure calibration) |
| !a(b) | Cancel calibration on pump A (B) |
| rxxxxx | Set total flow rate (A + B) |
| =xx | Set percent B |
| cala | Calibrate pump A |
| calb | Calibrate pump B |
| daxxxxx | Dispense pump A at rate xxxxxx (nl/min-valve switches automatically to dispense line) |
| dbxxxxx | Dispense pump B at rate xxxxxx (nl/min-valve switches automatically to dispense line) |
| faxxxxx | Fill pump A (nl/min-valve switches automatically to fill line) |
| fbxxxxx | Fill pump B (nl/min-valve switches automatically to fill line) |
| go | Start gradient (needs to be programmed first-see next section) |
| homea | Home pump A |
| homeb | Home pump B |
| list | List gradient program |
| m1 | Set output marker (1 is TTL low from rear port) |
| paxxxxx | Purge A pump with xxxxxnl per stroke |
| pbxxxxx | Purge B pump with xxxxxnl per stroke |
| <a(b) | Cancel purge on pump A (B) |
| qa1(0) | Enable (disable) PID on pump A |
| qb1(0) | Enable (disable) PID on pump B |
| sas | Stop pump A |
| saxxxx | Set pump A rate to xxxxnl/min (valve does not switch) |
| sbs | Stop pump B |
| sbxxxx | Set pump B rate to xxxxnl/min (valve does not switch) |
| tx.xx | Set time constant for flow rate buffer (0.1-5) |
| vaf | Set valve A to Fill |
| vac | Set valve A to Column |
| val | Set valve A to Waste |
| vbf | Set valve B to fill |

TABLE 2-continued

| Command | Action |
|---|---|
| vbc | Set valve A to Column |
| vb1 | Set valve A to Waste |
| xaxxxxx | Set first calibration constant for pump A |
| yaxxxxx | Set second calibration constant for pump A |
| zaxxxxx | Set third calibration constant for pump A |
| xbxxxxx | Set first calibration constant for pump B |
| ybxxxxx | Set second calibration constant for pump B |
| zbxxxxx | Set third calibration constant for pump B |
| [ | Begin download of gradient program |
| ] | End download of gradient program |
| \| | Stop gradient |
| % xx | Set percent B |

As noted, the gradient system 800 can be pre-programmed with computer software to operate autonomously after a series of time-based commands have been downloaded to the system 800. This methodology is termed gradient programming. There are several commands that may be used in a gradient program in addition to the ones listed in the previous section; illustrative examples of such commands are provided in Table 3.

TABLE 3

| Command | Action |
|---|---|
| %xx | Set percent B |
| m1 | Output high marker from rear of unit |
| a1 | Wait for trigger input on rear of unit |
| O1(0) | Set the output line to high (low) |
| wait | Wait |
| loop | Loop to beginning |
| rxxxx | Set total output rate to xxxx |

Figures 10, 11:
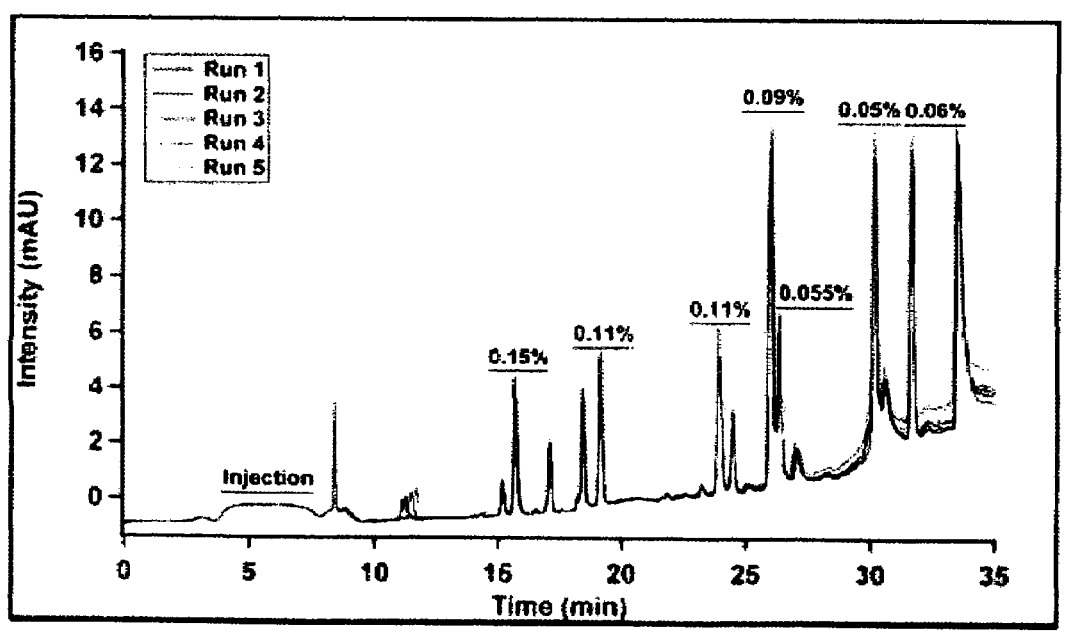
FIG. 10 is a portion of a computer program used in a system in accordance with an embodiment of the present invention.
FIG. 11 is a diagram illustrating results obtained with a system in accordance with the present invention.

Each of the commands in Table 3 can be programmed with the addition of time for the respective action. An example of a gradient program 300 of one embodiment of the invention is shown in FIG. 10. As shown in FIG. 10, in program 1000, the program 1000 sets the total output rate to 300 nl/min, and then waits for an input trigger. After the trigger, the system 800 linearly increases the percentage of B delivered from 0% to 50% over a period of 1798 seconds. After arriving at 50% B, the system 800 steps its rate to 90% B and delivers for a period of 600 seconds, then ramps down to 0% B over a period of 400 seconds. Once the ramp down is complete, the program 1000 is repeated. These commands may be sent to the system 800 via the RS-232 communication protocol, and the program 1000 is stored in the system 800 until the power is cycled or the program 1000 is overwritten.

The gradient system 800 may have two digital input/output (I/O) lines that can be used to synchronize the system 800 with external devices. One example is a TTL compatible (0-5V) digital input (not shown) that is used to trigger an event in the system's 800 internal program (using the wait trigger command above). Another example of a digital I/O line is a TTL-compatible digital output (not shown) that can be sent at any time during operation of the system 800 to signal an external device. Additional I/O lines can be added to the system 800 if required for a specific implementation.

Preferably, the gradient system 800 meets the following specifications:

| Specification | Details | Quantity | Units |
|---|---|---|---|
| Size | L × W × H | 8 × 8 × 5 | Inches |
| Weight | Dependent on design | 7 | Lbs |
| Power | Peak power | 24 VDC, 3 A | |
| Pump capacity | Per pump head | 250 | microliters |
| Delay volume | Dependent on external tubing length only | <300 | nanoliters |
| Proportioning steps | Relative change @ 300 nl/min | 0.2 | percent |
| Gradient reproducibility | % RSD on elution time for sequential 1-hour runs | <0.1 | percent |
| Flow rate range | | 0.05-4 | microliters per minute |
| Flow rate accuracy | | >98 | percent |
| Pressure range | | 346 | bar |
| Solvent compatibility | All solvents compatible with PEEK, stainless steel, zirconia, fused-silica, Perlast ®, and UHMW | Acetonitrile, water, methanol, ethanol, propanol | |
| Chemical resistance | All chemicals compatible with PEEK, stainless steel, zirconia, fused-silica, Perlast ®, and UHMW | TFA, acetic acid, formic acid, etc. | |
| Automated control | | yes | |
| Pressure reading | | 0-344 bar | |

The gradient system 800 provides extremely precise flow outputs from both the A and B pumps 885, 887, respectively, providing the excellent chromatographic separations shown in FIG. 11. These data represent five overlaid 1-hour chromatographic runs performed at 300 nl/min. The percent relative standard deviation (% RSD) for elution time between runs is shown in FIG. 11 for many of the peaks in a peptide mixture. RSD values in FIG. 11 were calculated by taking the absolute standard deviation in elution time of a given peak for all runs, then dividing by the average elution time for that peak. These % RSD numbers indicate absolute variability in retention time of only 0.6-1.2 seconds over the entire run.

This peptide sample consisted of a tryptic digest of cytochrome c dissolved in water with 0.05% TFA as additive. These experiments were conducted at a total flow rate of 300 nl/min with an injection volume of 1 nl. For these experiments, the pump A 885 solvent consisted of 5% ACN/water with 0.05% TFA, and the pump B 887 solvent consisted of 80% ACN/water with 0.04% TFA. The gradient profile was linearly ramped from 0-50% B over thirty minutes, followed by a wash at 80% B for 10 minutes. Prior to new injections, the column was re-equilibrated at 0% B for the balance of an hour.

The column used was a 75 μm ID×15 cm long PepMap™ nano-column packed with 3 μm C18 stationary phase, and detection was performed at 220 nm using the LC Packings' UltiMate UV detector module. This high level of run-to-run precision in FIG. 11 represents a significant improvement (5-10 fold) over conventional instruments. The data shown in FIG. 11 indicate that overall relative precision increases with time during the run. The type of sample separation shown in FIG. 11 is typical for Proteomics analyses, and indicates that the system 800 is amenable to real world applications.

FIG. 12 shows the output flow rates for both pump units 885, 887 over four sequential chromatographic runs performed on the nano-column used above with system 800. In FIG. 12, the flow rate obtained from pump A (885) is shown in blue and the flow rate from pump B (887) is shown in red. The total output rate was 300 nl/min. The gradient ramp portions of these experiments show excellent flow rate linearity with a residual error ($r^2$) of 0.9999.

FIG. 12 shows variability in flow rate output for this series of experiments of less than 0.01% RSD run-to-run. This estimate of precision is calculated by taking the standard deviation in the average flow rate for the 0% B region over sequential runs, and then dividing by the average flow rate.

FIG. 13 shows the system 800 responses to step changes in the desired flow rate on the gradient system 800. This experiment (the result of which are shown in FIG. 13) was conducted with a short length of narrow-bore capillary tubing inline with the gradient system 800 outlet 880, providing the flow-dependent backpressures indicated in FIG. 13. The achieved rates represent the mathematical average of the actual flow sensor output for the period of the step change. It should be noted that the desired and achieved rates are precise to within 0.01%.

For each of the rate levels shown in FIG. 13, the achieved (measured) output rate remains constant even though the system 800 backpressure is changing. This flow rate performance is a product of flow feedback and is not achievable with conventional split flow systems. In system 800, flow rate change requires approximately 10 seconds.

FIG. 14 depicts a step change in flow rate of 1 nl/min performed at 300 nl/min with system 800. These data are indicative of the resolution achievable with system 800. In FIG. 14, the desired rate is the average flow rate as measured by the flow sensors 820, 822 of the system 800. The desired step change (1 nl/min) and the achieved (measured) step change are within 0.009 nl/min.

The foregoing description of the invention is of the preferred embodiments and should not be considered a limitation on the scope of the invention claimed. Those skilled in the art will appreciate that changes may be made in the use of specific components, solutions, sample sizes, flow rates, and the like without departing from the spirit of the invention and the scope of the claims.

I claim:

1. An article of manufacture comprising: an electronic storage device comprising computer software having program instructions directing a computer running said instructions to receive and store in memory a first value for a first flow rate transmitted from a microfluidic flow sensor, receive and store in memory a second value for a second flow rate transmitted from said flow sensor, receive and store in memory a third value for a third flow rate transmitted from said flow sensor, and calculating values for constants a, b, and c corresponding to said first, second and third values for calibration of said flow sensor, wherein said program instructions further direct the computer to adjust the flow rate of a pump responsive to the flow rate calculated using the values calculated for constants a, b, and c.

2. The article according to claim 1 wherein said article comprises a hard disk.

3. The article according to claim 1 wherein said article comprises a CDROM.

4. The article according to claim 1 wherein said article comprises a non-volatile computer memory device.

5. A method of controlling flow rate in an analytical system comprising a pump in fluid communication with a flow sensor, comprising the steps of:
   a) pumping a fluid in the system at (n+1) preselected flow rates;
   b) determining the corresponding value for each flow rate from the flow sensor;
   c) calculating n constants for a polynomial equation with n as the highest order;
   d) measuring a flow rate from the flow sensor;
   e) calculating a real flow rate corresponding to the measured flow rate using the polynomial equation; and
   f) adjusting the pump velocity based on the calculated real flow rate.

6. The method of claim 5, wherein the analytical system comprises a mass spectrometry, microflow chromatography, nanoflow chromatography, nano-scale liquid chromatography, capillary electrophoresis, or reverse-phase gradient chromatography system.

* * * * *